(12) United States Patent
Salaita et al.

(10) Patent No.: US 10,905,710 B2
(45) Date of Patent: Feb. 2, 2021

(54) PARTICLES WITH RNA CLEAVING NUCLEOBASE POLYMERS AND USES FOR MANAGING INFLAMMATORY DISORDERS

(71) Applicants: Emory University, Atlanta, GA (US); The United States Government as represented by the Department of Veterans Affairs, Washington, DC (US)

(72) Inventors: Khalid Salaita, Decatur, GA (US); Cherry Wongtrakool, Atlanta, GA (US); Kornelia Galior, Rochester, MN (US)

(73) Assignees: Emory University, Atlanta, GA (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/304,549

(22) PCT Filed: May 24, 2017

(86) PCT No.: PCT/US2017/034268
§ 371 (c)(1),
(2) Date: Nov. 26, 2018

(87) PCT Pub. No.: WO2017/205506
PCT Pub. Date: Nov. 30, 2017

(65) Prior Publication Data
US 2019/0192550 A1 Jun. 27, 2019

Related U.S. Application Data

(60) Provisional application No. 62/340,586, filed on May 24, 2016.

(51) Int. Cl.
| | | |
|---|---|---|
| *A61K 31/713* | (2006.01) | |
| *A61K 31/712* | (2006.01) | |
| *C07H 21/04* | (2006.01) | |
| *A61K 9/00* | (2006.01) | |
| *A61K 9/51* | (2006.01) | |
| *A61P 11/06* | (2006.01) | |
| *A61K 9/14* | (2006.01) | |
| *A61K 45/06* | (2006.01) | |
| *B82Y 5/00* | (2011.01) | |

(52) U.S. Cl.
CPC ............ *A61K 31/713* (2013.01); *A61K 9/007* (2013.01); *A61K 9/008* (2013.01); *A61K 9/0073* (2013.01); *A61K 9/0075* (2013.01); *A61K 9/0078* (2013.01); *A61K 9/141* (2013.01); *A61K 9/51* (2013.01); *A61K 31/712* (2013.01); *A61K 45/06* (2013.01); *A61P 11/06* (2018.01); *B82Y 5/00* (2013.01); *C07H 21/04* (2013.01)

(58) Field of Classification Search
None
See application file for complete search history.

(56) References Cited

U.S. PATENT DOCUMENTS

| | | |
|---|---|---|
| 9,803,197 B2 | 10/2017 | Yehl |
| 2003/0064946 A1 | 4/2003 | McSwiggen |
| 2003/0125270 A1 | 7/2003 | Blatt |
| 2004/0092470 A1 | 5/2004 | Leonard |
| 2009/0028862 A1 | 1/2009 | Arndt |
| 2012/0009130 A1* | 1/2012 | Chakravarthy ...... A61K 31/713 424/43 |
| 2012/0029054 A1* | 2/2012 | Pickering ............. A61K 31/712 514/44 A |
| 2013/0030038 A1 | 1/2013 | Schmidts |
| 2014/0148396 A1 | 5/2014 | Zaragoza |
| 2017/0166890 A1* | 6/2017 | Carter ................ C12N 15/1131 |

FOREIGN PATENT DOCUMENTS

| | | | |
|---|---|---|---|
| WO | 2014003830 | 1/2014 | |
| WO | 2016184556 | 11/2016 | |
| WO | WO-2016184556 A1 * | 11/2016 | ............. A61K 45/06 |

OTHER PUBLICATIONS

Garn et al. GATA-3-specific DNAzyme—A novel approach for stratified asthma therapy, Eur J Immunol. 2017, 47 (1):22-30.
Hollenstein et al. DNA Catalysis: The Chemical Repertoire of DNAzymes, Molecules, 2015, 20, 20777-20804.
Homburg et al. Safety and tolerability of a novel inhaled GATA3 mRNA targeting DNAzyme in patients with TH2-driven asthma, J Allergy Clin Immunol, 2015, 136(3):797-800.
Homburg et al. Safety and tolerability of a novel inhaled GATA3 mRNA targeting DNAzyme in patients with TH2-driven asthma, J Allergy Clin Immunol, 2015, 136(3):797-800 (Supplmental Material).
Krug et al. Allergen-Induced Asthmatic Responses Modified by a GATA3-Specific DNAzyme, N Engl J Med 2015 2015, 372:1987-95.
Purath et al. Efficacy of T-cell transcription factor-specific DNAzymes in murine skin inflammation models, J Allergy Clin Immunol. 2016, 137(2):644-647.
Sel et al. Effective prevention and therapy of experimental allergic asthma using a GATA-3-specific DNAzyme, J Allergy Clin Immunol 2008,121:910-6.

(Continued)

*Primary Examiner* — Tracy Vivlemore
(74) *Attorney, Agent, or Firm* — Emory Patent Group

(57) ABSTRACT

This disclosure relates to nucleobase polymers useful for degrading GATA-3 mRNA. In certain embodiments, this disclosure relates to nucleobase polymers and nanoparticles conjugated to nucleobase polymers disclosed herein. In certain embodiments, the nucleobase polymers or nanoparticles can be used in methods of managing disorders associated with excessive GATA-3 expression in inflammatory disorders and respiratory disorders such as asthma.

11 Claims, 7 Drawing Sheets

Specification includes a Sequence Listing.

(56) References Cited

OTHER PUBLICATIONS

Somasuntharam et al., Knockdown of TNF-a by DNAzyme gold nanoparticles as an anti-inflammatory therapy for myocardial infarction, Biomaterials 83, 2016, 12-22.
Yehl et al. Catalytic Deoxyribozyme-Modified Nanoparticles for RNAi-Independent Gene Regulation, ACS Nano. 2012, 6(10): 9150-9157.

* cited by examiner

SEQUENCE LISTING

<160> NUMBER OF SEQ ID NOS: 55

<210> SEQ ID NO 1
<211> LENGTH: 31
<212> TYPE: DNA
<213> ORGANISM: Artificial
<220> FEATURE:
<223> OTHER INFORMATION: Synthetic

<400> SEQUENCE: 1
tgggcttaag gctagctaca acgagagggg c                               31

<210> SEQ ID NO 2
<211> LENGTH: 31
<212> TYPE: DNA
<213> ORGANISM: Artificial
<220> FEATURE:
<223> OTHER INFORMATION: Synthetic

```
<400> SEQUENCE: 2
tggtctgagg ctagctacaa cgaagttcgc a                               31

<210> SEQ ID NO 3
<211> LENGTH: 34
<212> TYPE: DNA
<213> ORGANISM: Artificial
<220> FEATURE:
<223> OTHER INFORMATION: Synthetic

<400> SEQUENCE: 3
gtctgttaat aggctagcta caacgatgtg aagc                            34

<210> SEQ ID NO 4
<211> LENGTH: 32
<212> TYPE: DNA
<213> ORGANISM: Artificial
<220> FEATURE:
<223> OTHER INFORMATION: Synthetic

<400> SEQUENCE: 4
tgctagacag gctagctaca acgattttcg gt                              32

<210> SEQ ID NO 5
<211> LENGTH: 33
<212> TYPE: DNA
<213> ORGANISM: Artificial
<220> FEATURE:
<223> OTHER INFORMATION: Synthetic

<400> SEQUENCE: 5
tttgctagag gctagctaca acgaattttt cgg                             33

<210> SEQ ID NO 6
<211> LENGTH: 33
<212> TYPE: DNA
<213> ORGANISM: Artificial
<220> FEATURE:
<223> OTHER INFORMATION: Synthetic

<400> SEQUENCE: 6 cttttttggag gctagctaca acgattgcta gac                            33

<210> SEQ ID NO 7
<211> LENGTH: 34
<212> TYPE: DNA
<213> ORGANISM: Artificial
<220> FEATURE:
<223> OTHER INFORMATION: Synthetic

<400> SEQUENCE: 7 tttttttgcag gctagctaca acgatttttg gatt                           34

<210> SEQ ID NO 8
<211> LENGTH: 32
<212> TYPE: DNA
<213> ORGANISM: Artificial
<220> FEATURE:
<223> OTHER INFORMATION: Synthetic

<400> SEQUENCE: 8
gcttcatgag gctagctaca acgaactgct cc                              32

<210> SEQ ID NO 9
```

<211> LENGTH: 32
<212> TYPE: DNA
<213> ORGANISM: Artificial
<220> FEATURE:
<223> OTHER INFORMATION: Synthetic

<400> SEQUENCE: 9
aggcttcagg ctagctacaa cgagatactg ct                                    32

<210> SEQ ID NO 10
<211> LENGTH: 33
<212> TYPE: DNA
<213> ORGANISM: Artificial
<220> FEATURE:
<223> OTHER INFORMATION: Synthetic

<400> SEQUENCE: 10
ggcttattca ggctagctac aacgaagatg ggg                                   33

<210> SEQ ID NO 11
<211> LENGTH: 33
<212> TYPE: DNA
<213> ORGANISM: Artificial
<220> FEATURE:
<223> OTHER INFORMATION: Synthetic

<400> SEQUENCE: 11
aatggcttag gctagctaca acgatcacag atg                                   33

<210> SEQ ID NO 12
<211> LENGTH: 33
<212> TYPE: DNA
<213> ORGANISM: Artificial
<220> FEATURE:
<223> OTHER INFORMATION: Synthetic

<400> SEQUENCE: 12 tagggatag gctagctaca acgagagtca gaa                                    33

<210> SEQ ID NO 13
<211> LENGTH: 33
<212> TYPE: DNA
<213> ORGANISM: Artificial
<220> FEATURE:
<223> OTHER INFORMATION: Synthetic

<400> SEQUENCE: 13
aataggggag gctagctaca acgaatgagt cag                                   33

<210> SEQ ID NO 14
<211> LENGTH: 34
<212> TYPE: DNA
<213> ORGANISM: Artificial
<220> FEATURE:
<223> OTHER INFORMATION: Synthetic

<400> SEQUENCE: 14
cactagagag gctagctaca acgacctgtt aaat                                  34

<210> SEQ ID NO 15
<211> LENGTH: 32
<212> TYPE: DNA
<213> ORGANISM: Artificial
<220> FEATURE:
<223> OTHER INFORMATION: Synthetic

<400> SEQUENCE: 15
tcacagcagg ctagctacaa cgatagagac cc					32

<210> SEQ ID NO 16
<211> LENGTH: 34
<212> TYPE: DNA
<213> ORGANISM: Artificial
<220> FEATURE:
<223> OTHER INFORMATION: Synthetic

<400> SEQUENCE: 16
tttttttcca ggctagctac aacgaagcac taga					34

<210> SEQ ID NO 17
<211> LENGTH: 34
<212> TYPE: DNA
<213> ORGANISM: Artificial
<220> FEATURE:
<223> OTHER INFORMATION: Synthetic

<400> SEQUENCE: 17
gttcagcagg ctagctacaa cgattttttt ttca					34

<210> SEQ ID NO 18
<211> LENGTH: 36
<212> TYPE: DNA
<213> ORGANISM: Artificial
<220> FEATURE:
<223> OTHER INFORMATION: Synthetic

<400> SEQUENCE: 18
atataagtta taggctagct acaacgagca atgttc					36

<210> SEQ ID NO 19
<211> LENGTH: 36
<212> TYPE: DNA
<213> ORGANISM: Artificial
<220> FEATURE:
<223> OTHER INFORMATION: Synthetic

<400> SEQUENCE: 19
caatataagt taggctagct acaacgaatg caatgt					36

<210> SEQ ID NO 20
<211> LENGTH: 33
<212> TYPE: DNA
<213> ORGANISM: Artificial
<220> FEATURE:
<223> OTHER INFORMATION: Synthetic

<400> SEQUENCE: 20
attccttaaa ggctagctac aacgattctt ggc					33

<210> SEQ ID NO 21
<211> LENGTH: 33
<212> TYPE: DNA
<213> ORGANISM: Artificial
<220> FEATURE:
<223> OTHER INFORMATION: Synthetic

<400> SEQUENCE: 21
ggaaacaaaa ggctagctac aacgatggca gtt					33

<210> SEQ ID NO 22
<211> LENGTH: 33
<212> TYPE: DNA

<213> ORGANISM: Artificial
<220> FEATURE:
<223> OTHER INFORMATION: Synthetic

<400> SEQUENCE: 22
gaaaggaaag gctagctaca acgaaaaact ggc        33

<210> SEQ ID NO 23
<211> LENGTH: 35
<212> TYPE: DNA
<213> ORGANISM: Artificial
<220> FEATURE:
<223> OTHER INFORMATION: Synthetic

<400> SEQUENCE: 23
ttttctttta aggctagcta caacgagcat caaac        35

<210> SEQ ID NO 24
<211> LENGTH: 33
<212> TYPE: DNA
<213> ORGANISM: Artificial
<220> FEATURE:
<223> OTHER INFORMATION: Synthetic

<400> SEQUENCE: 24
acaacaatta ggctagctac aacgaaggga ctt        33

<210> SEQ ID NO 25
<211> LENGTH: 34
<212> TYPE: DNA
<213> ORGANISM: Artificial
<220> FEATURE:
<223> OTHER INFORMATION: Synthetic

<400> SEQUENCE: 25
caaacaacaa ggctagctac aacgatacag ggac        34

<210> SEQ ID NO 26
<211> LENGTH: 35
<212> TYPE: DNA
<213> ORGANISM: Artificial
<220> FEATURE:
<223> OTHER INFORMATION: Synthetic

<400> SEQUENCE: 26
atacaaacaa ggctagctac aacgaaatta caggg        35

<210> SEQ ID NO 27
<211> LENGTH: 35
<212> TYPE: DNA
<213> ORGANISM: Artificial
<220> FEATURE:
<223> OTHER INFORMATION: Synthetic

<400> SEQUENCE: 27
tacatacaaa ggctagctac aacgaaacaa ttaca        35

<210> SEQ ID NO 28
<211> LENGTH: 35
<212> TYPE: DNA
<213> ORGANISM: Artificial
<220> FEATURE:
<223> OTHER INFORMATION: Synthetic

<400> SEQUENCE: 28
tgaattatac aggctagcta caacgaacaa acaac        35

<210> SEQ ID NO 29
<211> LENGTH: 36
<212> TYPE: DNA
<213> ORGANISM: Artificial
<220> FEATURE:
<223> OTHER INFORMATION: Synthetic

<400> SEQUENCE: 29
tttgaattat aggctagcta caacgaatac aaacaa                              36

<210> SEQ ID NO 30
<211> LENGTH: 33
<212> TYPE: DNA
<213> ORGANISM: Artificial
<220> FEATURE:
<223> OTHER INFORMATION: Synthetic

<400> SEQUENCE: 30
tcttttctta ggctagctac aacgatttgg tgc                                 33

<210> SEQ ID NO 31
<211> LENGTH: 37
<212> TYPE: DNA
<213> ORGANISM: Artificial
<220> FEATURE:
<223> OTHER INFORMATION: Synthetic

<400> SEQUENCE: 31
ataaatctac aggctagcta caacgacttt tcttatt                             37

<210> SEQ ID NO 32
<211> LENGTH: 36
<212> TYPE: DNA
<213> ORGANISM: Artificial
<220> FEATURE:
<223> OTHER INFORMATION: Synthetic

<400> SEQUENCE: 32
aaataaatct aggctagcta caacgaatct tttctt                              36

<210> SEQ ID NO 33
<211> LENGTH: 38
<212> TYPE: DNA
<213> ORGANISM: Artificial
<220> FEATURE:
<223> OTHER INFORMATION: Synthetic

<400> SEQUENCE: 33
tgtataatat gaggctagct acaacgagaa ataaatct                            38

<210> SEQ ID NO 34
<211> LENGTH: 37
<212> TYPE: DNA
<213> ORGANISM: Artificial
<220> FEATURE:
<223> OTHER INFORMATION: Synthetic

<400> SEQUENCE: 34
tctgtataat aggctagcta caacgagatg aaataaa                             37

<210> SEQ ID NO 35
<211> LENGTH: 35
<212> TYPE: DNA
<213> ORGANISM: Artificial
<220> FEATURE:

<223> OTHER INFORMATION: Synthetic

<400> SEQUENCE: 35
gtctgtataa ggctagctac aacgaatgat gaaat                                    35

<210> SEQ ID NO 36
<211> LENGTH: 34
<212> TYPE: DNA
<213> ORGANISM: Artificial
<220> FEATURE:
<223> OTHER INFORMATION: Synthetic

<400> SEQUENCE: 36
aatttataca aggctagcta caacgaagtt cggt                                     34

<210> SEQ ID NO 37
<211> LENGTH: 37
<212> TYPE: DNA
<213> ORGANISM: Artificial
<220> FEATURE:
<223> OTHER INFORMATION: Synthetic

<400> SEQUENCE: 37
aaataaattt ataggctagc tacaacgaaa cagttcg                                  37

<210> SEQ ID NO 38
<211> LENGTH: 36
<212> TYPE: DNA
<213> ORGANISM: Artificial
<220> FEATURE:
<223> OTHER INFORMATION: Synthetic

<400> SEQUENCE: 38
taaataaatt taggctagct acaacgaaca acagtt                                   36

<210> SEQ ID NO 39
<211> LENGTH: 36
<212> TYPE: DNA
<213> ORGANISM: Artificial
<220> FEATURE:
<223> OTHER INFORMATION: Synthetic

<400> SEQUENCE: 39
cagtaaataa aggctagcta caacgattat acaaca                                   36

<210> SEQ ID NO 40
<211> LENGTH: 35
<212> TYPE: DNA
<213> ORGANISM: Artificial
<220> FEATURE:
<223> OTHER INFORMATION: Synthetic

<400> SEQUENCE: 40
agcagtaaag gctagctaca acgaaaattt ataca                                    35

<210> SEQ ID NO 41
<211> LENGTH: 34
<212> TYPE: DNA
<213> ORGANISM: Artificial
<220> FEATURE:
<223> OTHER INFORMATION: Synthetic

<400> SEQUENCE: 41
gttcttaaga ggctagctac aacgatagca gtaa                                     34

<210> SEQ ID NO 42
<211> LENGTH: 34
<212> TYPE: DNA
<213> ORGANISM: Artificial
<220> FEATURE:
<223> OTHER INFORMATION: Synthetic

<400> SEQUENCE: 42
caaccaaaaa ggctagctac aacgatgaga gaga                              34

<210> SEQ ID NO 43
<211> LENGTH: 37
<212> TYPE: DNA
<213> ORGANISM: Artificial
<220> FEATURE:
<223> OTHER INFORMATION: Synthetic

<400> SEQUENCE: 43
ttagaagcta ggctagctac aacgattaat aaatatc                           37

<210> SEQ ID NO 44
<211> LENGTH: 32
<212> TYPE: DNA
<213> ORGANISM: Artificial
<220> FEATURE:
<223> OTHER INFORMATION: Synthetic

<400> SEQUENCE: 44
tgacatgcag gctagctaca acgagctggt ag                                32

<210> SEQ ID NO 45
<211> LENGTH: 32
<212> TYPE: DNA
<213> ORGANISM: Artificial
<220> FEATURE:
<223> OTHER INFORMATION: Synthetic

<400> SEQUENCE: 45
tcactaacag gctagctaca acgaagaaca cg                                32

<210> SEQ ID NO 46
<211> LENGTH: 34
<212> TYPE: DNA
<213> ORGANISM: Artificial
<220> FEATURE:
<223> OTHER INFORMATION: Synthetic

<400> SEQUENCE: 46
tgatcactaa ggctagctac aacgaacaga acac                              34

<210> SEQ ID NO 47
<211> LENGTH: 35
<212> TYPE: DNA
<213> ORGANISM: Artificial
<220> FEATURE:
<223> OTHER INFORMATION: Synthetic

<400> SEQUENCE: 47
attattccaa ggctagctac aacgaagact gtatt                             35

<210> SEQ ID NO 48
<211> LENGTH: 38
<212> TYPE: DNA
<213> ORGANISM: Artificial
<220> FEATURE:
<223> OTHER INFORMATION: Synthetic

```
<400> SEQUENCE: 48
aaatattttc aggctagcta caacgattta ttattatg                                38

<210> SEQ ID NO 49
<211> LENGTH: 36
<212> TYPE: DNA
<213> ORGANISM: Artificial
<220> FEATURE:
<223> OTHER INFORMATION: Synthetic

<400> SEQUENCE: 49
tagttttaaa aggctagcta caacgaattt tcactt                                  36

<210> SEQ ID NO 50
<211> LENGTH: 32
<212> TYPE: DNA
<213> ORGANISM: Artificial
<220> FEATURE:
<223> OTHER INFORMATION: Synthetic

<400> SEQUENCE: 50
tggatggagg ctagctacaa cgagtcttgg ag                                      32

<210> SEQ ID NO 51
<211> LENGTH: 15
<212> TYPE: DNA
<213> ORGANISM: Artificial
<220> FEATURE:
<223> OTHER INFORMATION: Synthetic

<400> SEQUENCE: 51
ggctagctac aacga                                                         15

<210> SEQ ID NO 52
<211> LENGTH: 3069
<212> TYPE: DNA
<213> ORGANISM: Homo sapiens

<400> SEQUENCE: 52
ggcgccgtct tgatactttc agaaagaatg cattccctgt aaaaaaaaaa aaaaaatact        60
gagagaggga gagagagaga gaagaagaga gagagacgga gggagagcga gacagagcga       120
gcaacgcaat ctgaccgagc aggtcgtacg ccgccgcctc ctcctcctct ctgctcttcg       180
ctacccaggt gacccgagga gggactccgc ctccgagcgg ctgaggaccc cggtgcagag       240
gagcctggct cgcagaattg cagagtcgtc gcccctttt acaacctggt cccgttttat        300
tctgccgtac ccagtttttg gattttgtc ttccccttct tctctttgct aaacgacccc       360
tccaagataa tttttaaaaa accttctcct ttgctcacct ttgcttccca gccttcccat       420
ccccccaccg aaagcaaatc attcaacgac ccccgaccct ccgacggcag gagccccccg       480
acctcccagg cggaccgccc tccctcccg cgcgcgggtt ccgggcccgg cgagagggcg        540
cgagcacagc cgaggccatg gaggtgacgg cggaccagcc gcgctgggtg agccaccacc       600
accccgccgt gctcaacggg cagcacccgg acacgcacca cccgggcctc agccactcct       660
acatggacgc ggcgcagtac ccgctgccgg aggaggtgga tgtgctttt aacatcgacg        720 gtcaaggcaa ccacgtcccg ccctactacg gaaactcggt cagggccacg gtgcagaggt       780
accctccgac ccaccacggg agccaggtgt gccgcccgcc tctgcttcat ggatccctac       840
cctggctgga cggcggcaaa gcctgggca gccaccacac cgcctccccc tggaatctca       900
gccccttctc caagacgtcc atccaccacg gctccccggg gcccctctcc gtctaccccc       960
```

```
cggcctcgtc ctcctccttg tcgggggcc acgccagccc gcacctcttc accttcccgc    1020
ccaccccgcc gaaggacgtc tccccggacc catcgctgtc caccccaggc tcggccggct    1080
cggcccggca ggacgagaaa gagtgcctca agtaccaggt gcccctgccc gacagcatga    1140
agctggagtc gtcccactcc cgtggcagca tgaccgccct gggtggagcc tcctcgtcga    1200
cccaccaccc catcaccacc tacccgcccct acgtgcccga gtacagctcc ggactcttcc    1260
cccccagcag cctgctgggc ggctccccca ccggcttcgg atgcaagtcc aggcccaagg    1320
cccggtccag cacagaaggc agggagtgtg tgaactgtgg ggcaacctcg accccactgt    1380
ggcggcgaga tggcacggga cactacctgt gcaacgcctg cgggctctat acaaaaatga    1440
acggacagaa ccggcccctc attaagccca agcgaaggct gtctgcagcc aggagagcag    1500
ggacgtcctg tgcgaactgt cagaccacca caaccacact ctggaggagg aatgccaatg    1560
gggaccctgt ctgcaatgcc tgtgggctct actacaagct tcacaatatt aacagacccc    1620
tgactatgaa gaaggaaggc atccagacca gaaaccgaaa aatgtctagc aaatccaaaa    1680
agtgcaaaaa agtgcatgac tcactggagg acttccccaa gaacagctcg tttaacccgg    1740
ccgccctctc cagacacatg tcctccctga gccacatctc gcccttcagc cactccagcc    1800
acatgctgac cacgcccacg ccgatgcacc cgccatccag cctgtccttt ggaccacacc    1860 accccctccag catggtcacc gccatgggtt agagccctgc tcgatgctca cagggccccc    1920
agcgagagtc cctgcagtcc ctttcgactt gcattttttgc aggagcagta tcatgaagcc    1980
taaacgcgat ggatatatgt ttttgaaggc agaaagcaaa attatgtttg ccactttgca    2040
aaggagctca ctgtggtgtc tgtgttccaa ccactgaatc tggacccccat ctgtgaataa    2100 gccattctga ctcatatccc ctatttaaca gggtctctag tgctgtgaaa aaaaaaatgc    2160
tgaacattgc atataactta tattgtaaga aatactgtac aatgacttta ttgcatctgg    2220
gtagctgtaa ggcatgaagg atgccaagaa gtttaaggaa tatgggagaa atagtgtgga    2280
aattaagaag aaactaggtc tgatattcaa atggacaaac tgccagtttt gtttcctttc    2340
actggccaca gttgtttgat gcattaaaag aaaataaaaa aagaaaaaa gagaaaagaa    2400 aaaaaagaa aaagttgta ggcgaatcat ttgttcaaag ctgttggcct ctgcaaagga    2460
aataccagtt ctgggcaatc agtgttaccg ttcaccagtt gccgttgagg gtttcagaga    2520 gccttttttct aggcctacat gctttgtgaa caagtccctg taattgttgt ttgtatgtat    2580
aattcaaagc accaaaataa gaaaagatgt agatttattt catcatatta tacagaccga    2640
actgttgtat aatttattta ctgctagtct taagaactgc tttctttcgt ttgtttgttt    2700
caatattttc cttctctctc aattttggt tgaataaact agattacatt cagttggcct    2760
aaggtggttg tgctcggagg gtttcttgtt tcttttccat tttgttttg gatgatattt    2820 attaaatagc ttctaagagt ccggcggcat ctgtcttgtc cctattcctg cagcctgtgc    2880 tgaggggtagc agtgtatgag ctaccagcgt gcatgtcagc gaccctggcc cgacaggcca    2940
cgtcctgcaa tcggcccggc tgcctcttcg ccctgtcgtg ttctgtgtta gtgatcactg    3000
cctttaatac agtctgttgg aataatatta taagcataat aataaagtga aaatatttta    3060
aaactacaa                                                             3069
```

<210> SEQ ID NO 53
<211> LENGTH: 33
<212> TYPE: DNA
<213> ORGANISM: Artificial
<220> FEATURE:

```
<223> OTHER INFORMATION: Synthetic

<400> SEQUENCE: 53
gtggatggag gctagctaca acgagtcttg gag                              33

<210> SEQ ID NO 54
<211> LENGTH: 31
<212> TYPE: DNA
<213> ORGANISM: Artificial
<220> FEATURE:
<223> OTHER INFORMATION: Synthetic

<400> SEQUENCE: 54
tggatggagg ctagctacaa cgagtcttgg a                                31

<210> SEQ ID NO 55
<211> LENGTH: 29
<212> TYPE: DNA
<213> ORGANISM: Artificial
<220> FEATURE:
<223> OTHER INFORMATION: Synthetic

<400> SEQUENCE: 55
ggatggaggc tagctacaac gagtcttgg                                   29
```

PARTICLES WITH RNA CLEAVING NUCLEOBASE POLYMERS AND USES FOR MANAGING INFLAMMATORY DISORDERS

CROSS-REFERENCE TO RELATED APPLICATIONS

This application is the National Stage of International Application No. PCT/US2017/034268 filed May 24, 2017, which claims the benefit of U.S. Provisional Application No. 62/340,586 filed May 24, 2016. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 16116US_ST25.txt. The text file is 14 KB, was created on Nov. 26, 2018, and is being submitted electronically via EFS-Web.

BACKGROUND

In asthma patients, airway obstruction is due to mucus secretion and airway inflammation. A number of medications can be used to treat asthma attacks, but managing persistent severe allergic asthma is problematic. Omalizumab is a recombinant humanized monoclonal antibody that specifically binds to human immunoglobulin E (IgE) and used in patients with severe persistent allergic asthma. However, systemic omalizumab administration may result in anaphylaxis or the generation of inactivating antibodies. Thus, there is a need to identify improved therapeutic methods to control persistent allergic asthma.

Allergic asthma results in T-helper (TH)-2 driven responses. Activation of TH2 cells produces cytokines such as IL-4, IL-5, and IL-13. Expression of these cytokines are dependent on the zinc finger transcription factor GATA-3. GATA-3 overexpression is observed in patients with severe asthma. Molecules that inactivate GATA-3 have been reported. See Sel et al. Effective prevention and therapy of experimental allergic asthma using a GATA-3-specific DNAzyme, J Allergy Clin Immunol. 2008, 121(4):910-916.

Krug et al. report allergen-induced asthmatic responses modified by a GATA-3-specific DNAzyme. The New England Journal of Medicine, 2015, 372(21):1987-1995. See also WO/2016/184556, WO/2014/040891, and WO/2005/033314.

Somasuntharam et al. report the knockdown of TNF-alpha by DNAzyme gold nanoparticles as an anti-inflammatory therapy for myocardial infarction. Biomaterials. 2016, 83:12-22. Yehl et al. report catalytic deoxyribozyme-modified nanoparticles for RNAi-independent gene regulation. ACS Nano. 2012, 6(10):9150-7.

References cited herein are not an admission of prior art.

SUMMARY

This disclosure relates to nucleobase polymers useful for degrading GATA-3 mRNA. In certain embodiments, this disclosure relates to nucleobase polymers and nanoparticles conjugated to nucleobase polymers disclosed herein. In certain embodiments, the nucleobase polymers or nanoparticles can be used in methods of managing disorders associated with excessive GATA-3 expression in inflammatory disorders and respiratory disorders such as asthma.

In certain embodiments, the disclosure relates to nucleobase polymers comprising or consisting of SEQ ID NO: 1-49, 53-55 or variants thereof.

In certain embodiments, the nucleobase polymer comprises
SEQ ID NO: 10 (GGCTTATTCAGGCTAGCTACAACGAAGATGGGG), SEQ ID NO: (ATTCCTTAAAGGCTAGCTACAACGATTCTTGGC), or SEQ ID NO: 30 (TCTTTTCTTAGGCTAGCTACAACGATTGGTGC) or variants thereof.

In certain embodiments, the disclosure contemplates a particle coated with or conjugated to a nucleobase polymer disclosed herein, e.g., SEQ ID NO: 1-51, 53-55 or variants thereof. In certain embodiments, the nucleobase polymers of disclose herein have an RNA cleaving sequence such as the 10-23 DNAzyme with SEQ ID NO: 51 (GGCTAGCTACAACGA), e.g., contained within SEQ ID NO: 1-50, 53-55. In certain embodiments, the cleaving sequence has monomers of 2-deoxyribose.

In certain embodiments, the variant is a nucleobase polymer comprising one nucleobase substitution, insertion, or deletion. In certain embodiments, the variant is a nucleobase polymer comprising two nucleobase substitutions, insertions, or deletions. In certain embodiments, the variant is a nucleobase polymer comprising three or nucleobase substitutions, insertions, or deletions.

In certain embodiments, the variant is a nucleobase polymer comprising one 5' end nucleobase substitution or deletion. In certain embodiments, the variant is a nucleobase polymer comprising two 5' end nucleobase substitutions or deletions. In certain embodiments, the variant is a nucleobase polymer comprising three 5' end nucleobase substitutions or deletion.

In certain embodiments, the variant is a nucleobase polymer comprising one 3' end nucleobase substitutions or deletions. In certain embodiments, the variant is a nucleobase polymer comprising two 3' end nucleobase substitutions or deletions. In certain embodiments, the variant is a nucleobase polymer comprising three 3' end nucleobase substitutions or deletions.

In certain embodiments, the disclosure relates to particles coated with a nucleobase polymer comprising an RNA cleaving sequence such as a nucleobase polymer comprising SEQ ID NO: 51 (GGCTAGCTACAACGA) and linked to flanking 5' and 3' nucleobases that hybridize with SEQ ID NO: 52.

In certain embodiments, the particle or nanoparticle has a core or hydrodynamic diameter between 5 nm and 500 nm or 5 nm and 200 nm. In certain embodiments, the particle may contain a metal or inorganic or polymer core. In certain embodiments, conjugation to a particle can be accomplished by using linking groups with ligands, e.g., mono or polydentate ligands, capable of binding the metal in the core or by direct conjugation through covalent bonds of a polymer surrounding and encapsulating the core. In certain embodiments, the nucleobase polymer may further contain a targeting nucleobase polymer sequence or targeting nucleic acid sequence that can hybridize with a target sequence coated on the exterior of the particle.

In certain embodiments, the disclosure relates to aerosols, liquid particles, mixtures or gas and liquid particles, comprising a nucleobase polymer or a particle disclosed herein.

In certain embodiments, the liquid particle has a diameter of between 1 microns and 5 microns, 0.5 microns and 10 microns, 0.1 microns and 50 microns, or 0.5 microns and 100 microns.

In certain embodiments, this disclosure relates to a nucleobase polymer or a particle disclosed herein in the form of a micronized powder, e.g., solid particles of a diameter between 1 microns and 5 microns, 0.5 microns and 10 microns, 0.1 microns and 50 microns, or 0.5 microns and 100 microns.

In certain embodiments, this disclosure relates to pharmaceutical composition comprising a nucleobase polymer disclosed herein or a particle disclosed herein and a pharmaceutically acceptable excipient. In certain embodiments, the pharmaceutical composition comprises a sterilized pH buffered aqueous salt solution or an isotonic aqueous buffer solution.

In certain embodiments, the disclosure relates to a container, optionally sealed gas tight, comprising a nucleobase polymer or particle disclosed herein. In certain embodiments, the container further comprises a propellant. In certain embodiments, the container is configured with a spraying or misting apparatus, mouthpiece, or facemask such as a nebulizer or inhaler. In certain embodiments, the inhaler comprises a liquefied gas propellant. In certain embodiments, the nucleobase polymer or particle is dissolved or suspended in the propellant. In certain embodiments, the inhaler is configured with an actuator or mouthpiece, which allows the patient to operate the device, and directs the aerosol, a chamber, and metering value that controls a metered quantity of a formulation to be dispensed with an actuation.

In certain embodiments, the disclosure relates to methods of treating an inflammatory disease comprising administering an effective amount of a nucleobase polymer or particle disclosed herein to a subject in need thereof. In certain embodiments, the inflammatory disease is a respiratory disorder, asthma, COPD, atopic dermatitis, psoriasis, or ulcerative colitis. In certain embodiments, the subject is diagnosed with, exhibiting symptoms of or at risk of asthma, COPD, bronchitis, emphysema, chronic obstructive pulmonary disease, laryngitis, or cystic fibrosis.

In certain embodiments, administration is in combination with a second respiratory agent. In certain embodiments, the second respiratory agent is a corticosteroid, bronchodilator, albuterol, ipratropium, or combinations thereof.

DETAILED DISCUSSION

Figure 1:
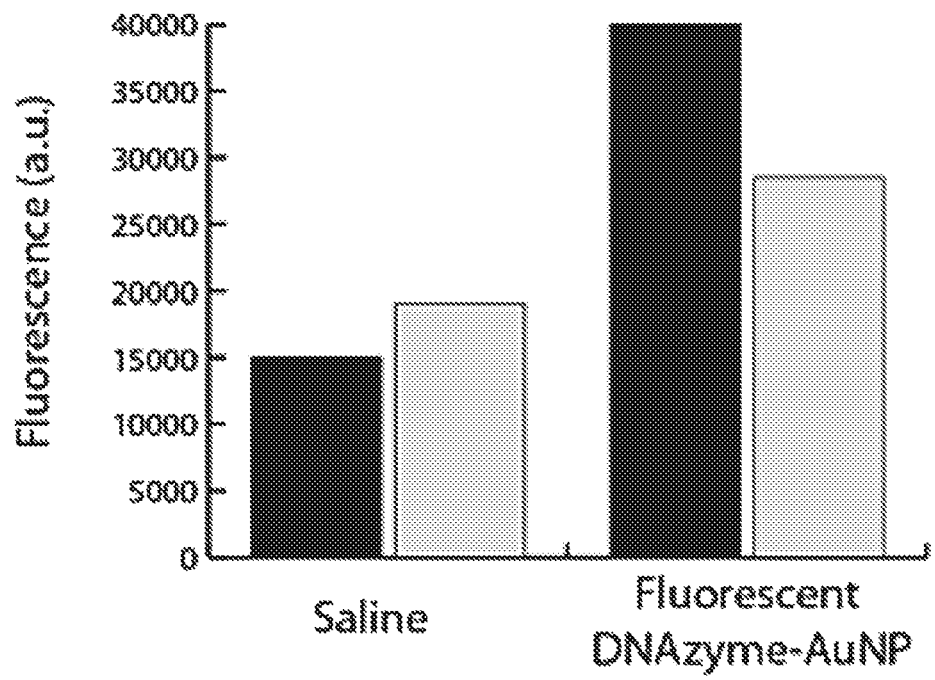
FIG. 1 shows a plot quantifying inhaled delivery of GATA-3 DzNPs using fluorescence imaging. GATA-3 DzNPs were nebulized with even and distal distribution in the lung. Vehicle (phosphate buffered saline, 50 µl of) and 50 µl of fluorescently tagged DzNPs (100 nM, two lungs on right) were administered to mice by nebulization into 4-6 µm sized aerosol droplets using a bias flow of 2 liters/min of room air. Imaging was performed 24 hours following delivery.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The transitional term "comprising", which is synonymous with "including," "containing," or "characterized by," is inclusive or open-ended and does not exclude additional, unrecited elements or steps, e.g., does not exclude the presence of terminal nucleotides. The transitional phrase "consisting of" excludes any additional nucleotides, elements, steps, or ingredients not specified in the claim.

As used herein, the term "combination with" when used to describe administration with an additional treatment means that the agent may be administered prior to, together with, or after the additional treatment, or a combination thereof.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g., patient) is cured and the condition or disease is eradicated. Rather, embodiments, of the present disclosure also contemplate treatment that merely reduces symptoms, and/or delays conditions or disease progression.

As used herein, the term "nucleic acid" is intended to mean a ribonucleic or deoxyribonucleic acid or analog thereof, including a nucleic acid analyte presented in any context; for example, a probe, target or primer. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. Exemplary non-native bases that can be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which base-pairs with cytosine, adenine or uracil. Alternatively or additionally, oligonucleotides, nucleotides or nucleosides including the above-described non-native bases can further include reversible blocking groups on the 2', 3' or 4' hydroxyl of the sugar moiety.

The terms "binding," "binds," "recognition," or "recognize" as used herein are meant to include interactions between molecules that may be detected using, for example, a hybridization assay. When hybridization occurs in an antiparallel configuration between two single-stranded polynucleotides, the reaction is called "annealing" and those polynucleotides are described as "complementary". A double-stranded polynucleotide can be complementary or homologous to another polynucleotide, if hybridization can occur between one of the strands of the first polynucleotide and the second. Complementarity or homology (the degree that one polynucleotide is complementary with another) is quantifiable in terms of the proportion of bases in opposing strands that are expected to form hydrogen bonding with each other, according to generally accepted base-pairing rules.

A "linking group" refers to any variety of molecular arrangements that can be used to bridge to molecular moieties together. An example formula may be -Rm- wherein R is selected individually and independently at each occurrence as: —CRmRm-, —CHRm-, —CH—, —C—, —CH2-, —C(OH)Rm, —C(OH)(OH)—, —C(OH)H, —C(Hal)Rm-, —C(Hal)(Hal)-, —C(Hal)H—, —C(N3)Rm-, —C(CN)Rm-, —C(CN)(CN)—, —C(CN)H—, —C(N3)(N3)—, —C(N3)H—, —O—, —S—, —N—, —NH—, —NRm-, —(C═O)—, —(C═NH)—, —(C═S)—, —(C═CH2)—, which may contain single, double, or triple bonds individually and independently between the R groups. If an R is branched with an Rm it may be terminated with a group such as —CH3, —H, —CH=CH2, —CCH, —OH, —SH, —NH2, —N3, —CN, or -Hal, or two branched Rs may form a cyclic structure. It is contemplated that in certain instances, the total Rs or "m" may be less than 100 or 50 or 25 or 10. Examples of linking groups include bridging amide, alkyl, and alkoxyalkyl groups.

Targeting the Transcription Factor GATA-3 to Modulate the Inflammatory Response

The most prevalent type of asthma (50% of patients) displays a type 2 helper T cell (Th2) endotype, which is characterized by an overabundance of Th2 cells that express inflammatory cytokines such as 11-4, 11-5, and 11-13. GATA-3 is the major transcription factor involved in driving differentiation of helper T cells toward the Th2 fate. Moreover, GATA-3 has been found to be upregulated in biopsies and serum from patients with severe asthma, even while on oral corticosteroids. GATA-3 is expressed in resident lung cell types, such as mast cells, eosinophils, macrophages, fibroblasts, and airway epithelial cells.

Inhibiting GATA-3 production by gene knockdown has been shown to suppress upregulation of cytokines and prevent the induction of airway hyper-responsiveness amongst other asthma symptoms. A recent phase II clinical trial demonstrated that administering GATA-3 DNAzymes (Dzs) by inhalation can reduce the impact of an allergen challenge on FEV1 (forced expiratory volume) in mild asthmatics. After treatment with Dz targeting GATA-3, both the early and late asthmatic responses are attenuated, improving overall airway function. This emphasized the importance of GATA-3 in regulating the asthmatic response. However, allowing an oligonucleotide to pass across the plasma membrane is challenging. Accordingly, clinical trials require 2 mg doses of oligonucleotides per patient per day.

Dzs are synthetic, catalytically active DNA antisense molecules that bind to and cleave specific mRNA. They possess a central catalytic domain that typically ranges from 8-15 nucleotides. Flanking this site are two variable domains, typically 8-12 nucleotides each that can be designed to hybridize to the mRNA molecule of interest. By screening sites in the GATA-3 mRNA, a highly active Dzs were discovered that target and cleave the GATA-3 gene. Cytoplasmic RNAses further degrade the cleavage products.

To overcome the challenges of delivering Dzs as gene regulation agents, Dz nanoparticle conjugates were developed for gene regulation. Copies of Dz molecules immobilized onto a 14 nm gold nanoparticle (DzNP) through the 3' terminus are highly active for mRNA knock down. These particles can rapidly enter cells, protect the DNAzyme against nucleases, and regulate gene expression in vitro. DzNPs show minimal off-target effects and did not require the use of any transfection agents. Therefore, DzNPs offer an attractive approach for delivering catalytic nucleic acids to treat disease.

GATA-3 mRNA and Nucleobase Polymers Containing DNAzyme Sequences

*Homo sapiens* GATA binding protein 3 (GATA-3), transcript variant 1, mRNA has the NCBI Reference Sequence NM_001002295.1 (SEQ ID NO: 52):

GGCGCCGTCTTGATACTTTCAGAAAGAATGCATTCCCTGTAAAAAAAAAAA AAAATACTGAGAGAGGGAGAGAGAGAGAGAAGAAGAGAGAGAGACGGAGGGAGA GCGAGACAGAGCGAGCAAC-GCAATCTGACCGAGCAGGTCGTACGCCGCCGCCT-CCT CCTCCTCTCTGCTCTTCGCTACCCAGGTG- ACCCGAGGAGGGACTCCGCCTCCGAGCG GCT-GAGGGACCCCGGTGCAGAGGAGCCTGGCTCG-CAGAATTGCAGAGTCGTCGCCCC TTTTTACAAC-CTGGTCCCGTTTTATTCTGCCGTACCCAGTTTTTG-GATTTTTGTCTTCC CCTTCTTCTCTTTGCTAAA-CGACCCCTCCAAGATAATTTTTAAAAAACCT-TCTCCTTT GCTCACCTTTGCTTCCCAGCCTTCC-CATCCCCCCACCGAAAGCAAATCATTCAACGA CCCCCGACCCTCCGACGGCAGGAGCCCCCC-GACCTCCCAGGCGGACCGCCCTCCCTC CCCGC-GCGCGGGTTCCGGGCCCGGCGAGAGGGCGCGA-GCACAGCCGAGGCCATGG AGGTGACGGCGG-ACCAGCCGCGCTGGGTGAGCCACCACCACCCC-GCCGTGCTCAAC GGGCAGCACCCGGACACGCAC-CACCCGGGCCTCAGCCACTCCTACATGGACGCGGC GCAGTACCCGCTGCCGGAGGAGGTGGATGTGCT-TTTTAACATCGACGGTCAAGGCA ACCACGTCCC-GCCCTACTACGGAAACTCGGTCAGGGCCACGGT-GCAGAGGTACCCT CCGACCCACCACGGGAGCCA-GGTGTGCCGCCCGCCTCTGCTTCATGGATCCC-TACCC TGGCTGGACGGCGGCAAAGCCCTGGGC-AGCCACCACACCGCCTCCCCCTGGAATCT CAGCCCCTTCTCCAAGACGTCCATCCAC-CACGGCTCCCCGGGGCCCCTCTCCGTCTA CCCCCCGGCCTCGTCCTCCTCCTTGTCGGGGGGC-CACGCCAGCCCGCACCTCTTCAC CTTCCCGCC-CACCCCGCCGAAGGACGTCTCCCCGGACC-CATCGCTGTCCACCCCAGG CTCGGCCGGCTCGG-CCCGGCAGGACGAGAAAGAGTGCCTCAAGTACC-AGGTGCCCC TGCCCGACAGCATGAAGCTGGAGT-CGTCCCACTCCCGTGGCAGCATGACCGCCCTG GGTGGAGCCTCCTCGTCGACCCACCACCCCATCAC-CACCTACCCGCCCTACGTGCCC GAGTACAGCTC-CGGACTCTTCCCCCCCAGCAGCCTGCTGGGCGG-CTCCCCCACCGGC TTCGGATGCAAGTCCAGGCC-CAAGGC- CCGGTCCAGCACAGAAGGCAGG-GAGTGTGT GAACTGTGGGGCAACCTCGACCC-CACTGTG- GCGGCGAGATGGCACGGGACACTACC TGTGCA- ACGCCTGCGGGCTCTATCACAAAAT-GAACGGAC- AGAACCGGCCCCTCATT AAGCC-CAAGCGAA- GGCTGTCTGCAGCCAG-GAGAGCAGGGACGTC- CTGTGCGAACTG TCAGACCACCACAACCACACT- CTGGAGGAG-GAATGCCAATGGGGACCCTGTCTGCA ATGCCTGTGGGCTCTACTACAAGCTTCACAATAT-TAACAGACCCCTGACTATGAAGA AGGAAGG-CATCCAGACCAGAAACCGAAAAATGTCTAGCAA-ATCCAAAAAGTGCAA AAAAGTGCATGACTCACTG-GAGGACTTCCCCAAGAACAGCTCGTTTAACCC-GGCCG CCCTCTCCAGACACATGTCCTCCCTGAGC-CACATCTCGCCCTTCAGCCACTCCAGCC ACATG-CTGACCACGCCCACGCCGATGCACCCGCCATCC-AGCCTGTCCTTTGGACCAC ACCACCCCTCCAG-CATGGTCACCGCCATGGGTTAGAGCCCTGCTC-GATGCTCACAGG GCCCCAGCGAGAGTCCCT-GCAGTCCCTTTCGACTTGCATTTTGCAG-GAGCAGTAT CATGAAGCCTAAACGCGATGGA-TATATGTTTTTGAAGGCAGAAAGCAAAATTATGTT TGCCACTTTGCAAAGGAGCTCACTGTGGTG-TCTGTGTTCCAACCACTGAATCTGGAC CCCATCTG-TGAATAAGCCATTCTGACTCATATCCCCTATT-TAACAGGGTCTCTAGTGC TGTGAAAAAAAA-AATGCTGAACATTGCATATAACTTATATTGTAAG-AAATACTGTAC AATGACTTTATTGCATCTGGGTA-GCTGTAAGGCATGAAGGATGCCAAGAAGTTTAAG GAATATGGGAGAAATAGTGTGGAAAT-TAAGAAGAAACTAGGTCTGATATTCAAATG

GACAAACTGCCAGTTTTGTTTCCTTTCACTGGC-
CACAGTTGTTTGATGCATTAAAAGA AAATAAAAA-
AAAGAAAAAAGAGAAAAGAAAAAAAAAGAAA-
AAAGTTGTAGGCGA ATCATTTGTTCAAAGCTG-
TTGGCCTCTGCAAAGGAAATACCAGTTCTG-
GGCAATCAG TGTTACCGTTCACCAGTTGCCGTT-
GAGGGTTTCAGAGAGCCTTTTTCTAGGCCTACAT
GCTTTGTGAACAAGTCCCTGTAATTGTTGTTT-
GTATGTATAATTCAAAGCACCAAAA TAAGAAAA-
GATGTAGATTTATTTCATCATATTATACAGACCG-
AACTGTTGTATAATT TATTTACTGCTAGTCT-
TAAGAACTGCTTTCTTTCGTTTGTTTGTTTCAATAT-
TTTCCTT CTCTCTCAATTTTTGGTTGAATAAACTA-
GATTACATTCAGTTGGCCTAAGGTGGTTGT GCTC-
GGAGGGTTTCTTGTTTCTTTTCCATTTTGTTTTTG-
GATGATATTTATTAAATAGC TTCTAAGAGTCC-
GGCGGCATCTGTCTTGTCCCTATTCCTGCAGCC-
TGTGCTGAGGGTA GCAGTGTATGAGCTACCAG-
CGTGCATGTCAGCGACCCTGGCCCGACAGGC-
CACGTC CTGCAATCGGCCCGGCTGCCTCTTCGCCC-
TGTCGTGTTCTGTGTTAGTGATCACTGCC TTTAATA-
CAGTCTGTTGGAATAATATTATAAGCATAATAAT-
AAAGTGAAAATATTTT AAAACTACAA. The GATA-3
protein is encode by nucleotide 558-1892.

In certain embodiments, methods and compositions disclosed herein may be implemented with a nucleobase polymers comprising sequences that hybridizes or is the reverse complement to GATA-3 mRNA and contains an RNA cleaving nucleobase sequence such as a cleaving DNAzyme sequence. DNAzymes are catalytically active DNA molecules. DNAzyme 10-23 is DNA with two binding domains flanking a central catalytic domain. After binding of a DNAzyme to the corresponding sequence in the target mRNA via the binding domains, the catalytic domain cleaves the target mRNA molecule. The binding domains and catalytic domain may contain modifications provided they are capable of specifically binding the corresponding target mRNA of GATA-3. Schubert et al. report DNAzymes against the same target site that are stabilized by the use of a 3'-3'-inverted thymidine, phosphorothioate linkages, 2'-O-methyl RNA and locked nucleic acids. Nucleic Acids Res. 2003, 31(20): 5982-5992. In certain embodiments, methods and compositions disclosed herein may be implemented with a nucleobase polymers comprising units of a ribose, 2' deoxyribose, locked nucleic acids (1-(hydroxymethyl)-2,5-dioxabicyclo[2.2.1]heptan-7-01), 2'-O-methyl groups, a 3'-3'-inverted thymidine, phosphorothioate linkages, or combinations thereof.

The term "nucleobase polymer" refers to a molecule having nucleobase monomers capable of hybridizing to a single-stranded nucleic acid target. The nucleobase polymers that target GATA-3 mRNA typically comprise a sequence that is the reverse complement of, more than 7, 8, 9, 10, 11, 12, 13, 14, 15, 20, or more nucleotides or nucleobases or continuous nucleotide nucleobases of SEQ ID NO: 52. The targeting sequence of nucleobases is typically separated by an RNA cleaving sequence such as a DNAzyme sequence capable of forming a loop-like structure. The nucleobase polymer may be a single stranded nucleic acid or analog containing a sufficiently small number of target mismatches, additions, or deletions as long as the targeting sequences retain the ability to bind to the target RNA.

In certain embodiments, the nucleobase polymer including the targeting sequence and the RNA cleaving DNAzyme may be less than 500, 200, 100, 50, or 35 nucleotides or nucleobases. In certain embodiments, the disclosure contemplates the use of nucleobase polymers disclosed herein for disruption of GATA-3 expression.

Nucleobase monomers are typically nitrogen containing aromatic or heterocyclic bases that bind to naturally occurring nucleic acids through hydrogen bonding otherwise known as base pairing. A typical nucleobase polymer is a nucleic acid, RNA, DNA, or chemically modified form thereof. A nucleobase polymer may be single or double stranded or both, e.g., they may contain overhangs. Nucleobase polymers may contain naturally occurring or synthetically modified bases and backbones. In certain embodiments, a nucleobase polymer need not be entirely complementary, e.g., may contain one or more insertions, deletions, or be in a hairpin structure provided that there is sufficient selective binding.

With regard to the nucleobases, it is contemplated that the term encompasses isobases, otherwise known as modified bases, e.g., are isoelectronic or have other substitutes configured to mimic naturally occurring hydrogen bonding base-pairs, e.g., within any of the sequences herein U may be substituted for T, or T may be substituted for U. Examples of nucleotides with modified adenosine or guanosine include, but are not limited to, hypoxanthine, xanthine, 7-methylguanine. Examples of nucleotides with modified cytidine, thymidine, or uridine include 5,6-dihydrouracil, 5-methylcytosine, 5-hydroxymethylcytosine. Contemplated isobases include 2'-deoxy-5-methylisocytidine (iC) and 2'-deoxy-isoguanosine (iG) (see U.S. Pat. Nos. 6,001,983; 6,037,120; 6,617,106; and 6,977,161). In another embodiment, a removable base (such as uracil or 8-oxoguanine) is contemplated so that treatment by uracil-DNA glycosylase (UDG) or formamidopyrimidine-DNA glycosylase (FPG), can lead to cleavage and degradation of unwanted sequences.

In order to prevent in vivo breakdown nucleic acids may be chemically modified, e.g., within the sugar backbone or on the 5' or 3' ends. As such, in certain embodiments, nucleobase polymers disclosed herein may contain monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphon amidate, morpholin-2-yl-methanol, (2-(hydroxymethyl)morpholino) (piperazin-1-yl) phosphinate, or peptide nucleic acids or combinations thereof.

Within any of the sequences disclosed herein, U may be T or T may be U.

In certain embodiments, the nucleotide base polymer is single or double stranded DNA that is 3' end capped with one, two, or more thymidine nucleotides and/or a 5' end polyphosphorylated, e.g., di-phosphate, tri-phosphate.

In certain embodiments, the nucleobase polymer can be modified to contain a 3' end thiol group for direct absorption on gold or silver surfaces and particles. In certain embodiments, the nucleobase polymer is conjugated to a poly T sequence. In certain embodiments, the poly T sequence is on the 3' end of the nucleobase polymer. In certain embodiments, the poly T sequence has four or more repeating thymine (T) bases followed by a 3' end thiol group. In certain embodiments, the nucleobase polymer can be modified to contain a phosphodiester bond. Replacing one of the non-bridging oxygen by sulfur imparts resistance to nuclease degradation. In certain embodiments, the nucleobase polymer can be modified to contain a C-5 propyne substitution of dC and/or dT in the target sequences. In certain embodiments, the nucleobase polymer can be modified to contain a 2'-5' linkages and 2'-5' linked ends synthesized using 3'-deoxy-2'-phosphoramidites and 2'-deoxy-3'-phosphoramidites. In certain embodiments, the nucleobase polymer can be modified to contain a terminal 5'-5' or 3'-3' linkage. For the terminal 5'-5' linkage, the appropriate 5'-phosphoramidite is incorporated at the 5'-end in a synthesis cycle. For the terminal 3'-3' linkage, the appropriate deoxynucleoside-5'-CPG is used as the solid support for the 3'-end, followed by synthesis of the oligo in the standard 3'-5' direction to make the terminal 3'-3' linkage.

In certain embodiments, the disclosure relates to compounds, compositions, and methods disclosed herein using nucleobase polymers. In certain embodiment, nucleobase polymers may contain any of the sequences provided in the table 1 of the experimental section (SEQ ID NO: 1-49).

In certain embodiments, the disclosure contemplates that DNAzyme 10-23, SEQ ID NO: 51 (GGCTAGCTA-CAACGA) can be substituted with other DNAzymes sequences. The DNAzyme 10-23 is comprised of a sequence of DNA that will cleave mRNA strands that contain an unpaired purine-pyrimidine pair. The DNAzyme 10-23 is flanked by recognition sequences that hybridized to the regions of the target mRNA sequences adjacent to the unpaired purine-pyrimidine pair. Therefore, the DNAzyme hybridizes and cleaves at the purine-pyrimidine site.

In certain embodiments, this disclosure contemplates that the cleaving nucleic acids comprise sequences of DNAzymes 8-17 and 10-23. Santoro & Joyce disclosed a general purpose RNA-cleaving DNAzymes 8-17 and 10-23. See PNSA, 1997, 94 (9), 4262-4266.

In certain embodiments, this disclosure contemplates that the cleaving nucleic acids comprise amine, guanidine, imidazole modifications such as 8-imidazolyl modified deoxy adenosines. Perrin et al., disclose modified DNAzymes 20-49 containing amine, guanidine, and imidazole-modified dNTPs. Org Biomol Chem 2011, 9 (7), 2266-2273.

Synthesis of Nucleobases Polymers

Small nucleobase polymers and nucleic acid motifs ("small" refers to nucleic acid motifs no more than 100 nucleotides in length, preferably no more than 80 nucleotides in length, and most preferably no more than 50 nucleotides in length; e.g., individual oligonucleotide sequences or sequences synthesized in tandem) are preferably used for exogenous delivery. Exemplary molecules of the instant disclosure may be chemically synthesized or by the use of cellular or non-cellular expression systems. Nucleic acids made by cellular or non-cellular expression systems can be further modified.

One synthesizes oligonucleotides (e.g., certain modified oligonucleotides or portions of oligonucleotides) using protocols known in the art as, for example, described in U.S. Pat. No. 6,001,311. The synthesis of oligonucleotides makes use of common nucleic acid protecting and coupling groups, such as dimethoxytrityl at the 5'-end and phosphoramidites at the 3'-end.

In a non-limiting example, small scale syntheses are conducted on a 394 Applied Biosystems, Inc. synthesizer using a 0.2 micro mol scale protocol with a 2.5 min coupling step for 2'-O-methylated nucleotides and a 45 second coupling step for 2'-deoxy nucleotides or 2'-deoxy-2'-fluoro nucleotides. Alternatively, syntheses at the 0.2 micro mol scale can be performed on a 96-well plate synthesizer, such as the instrument produced by Protogene (Palo Alto, Calif.) with minimal modification to the cycle. A 33-fold excess of 2'-O-methyl phosphoramidite and a 105-fold excess of S-ethyl tetrazole can be used in each coupling cycle of 2'-O-methyl residues relative to polymer-bound 5'-hydroxyl. A 22-fold excess of deoxy phosphoramidite and a 70-fold excess of S-ethyl tetrazole mop can be used in each coupling cycle of deoxy residues relative to polymer-bound 5'-hydroxyl. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM 12, 49 mM pyridine, 9% water in THF (PerSeptive Biosystems, Inc.). S-Ethyltetrazole solution (0.25 M in acetonitrile) is made up from the solid obtained from American International Chemical, Inc. Alternately, for the introduction of phosphorothioate linkages, Beaucage reagent (3H-1,2-benzodithiol-3-one 1,1-dioxide, 0.05 M in acetonitrile) is used.

Deprotection of the DNA-based oligonucleotides is performed as follows: the polymer-bound trityl-on oligonucleotide is transferred to a 4 mL glass screw top vial and suspended in a solution of 40% aqueous methylamine (1 mL) at 65 degrees for 10 minutes. After cooling to −20 degrees, the supernatant is removed from the polymer support. The support is washed three times with 1.0 mL of EtOH:MeCN:H2O/3:1:1, vortexed and the supernatant is then added to the first supernatant. The combined supernatants, containing the oligonucleotide, are dried.

Alternatively, the nucleic acid molecules can be synthesized separately and joined together post-synthetically, for example, by ligation or by hybridization following synthesis and/or deprotection.

Nucleic acids can also be assembled from two distinct nucleic acid strands or fragments wherein one fragment includes the sense region and the second fragment includes the antisense region of the RNA molecule.

The nucleic acid molecules can be modified extensively to enhance stability by modification with nuclease resistant groups, for example, 2'-amino, 2'-C-allyl, 2'-fluoro, 2'-O-methyl, 2'-H). Constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See e.g., U.S. Pat. Nos. 5,652,094, 5,334,711, and 6,300,074. All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

In one embodiment, nucleic acid molecules include one or more (e.g., about 1, 2, 3, 4, 5, 6, 7, 8, 9, 10, or more) G-clamp nucleotides. A G-clamp is a tricyclic aminoethyl-phenoxazine 2'-deoxycytidine or analogue. See Lin &. Matteucci, J Am Chem Soc, 1998, 120, 8531-8532; Flanagan, et al., Proc Nat Acad Sci USA, 1999, 96, 3513-3518; and Maier, et al., Biochemistry, 2002, 41, 1323-1327. A single G-clamp analog substitution within an oligonucleotide can result in substantially enhanced helical thermal stability and mismatch discrimination when hybridized to complementary oligonucleotides. The inclusion of such nucleotides in nucleic acid molecules results in both enhanced affinity and specificity to nucleic acid targets, complementary sequences, or template strands.

In another embodiment, nucleic acid molecules include one or more (e.g., about 1, 2, 3, 4, 5, 6, 7, 8, 9, 10, or more)

LNA "locked nucleic acid" nucleotides such as a 2',4'-C methylene bicyclo nucleotide (see for example U.S. Pat. Nos. 6,639,059, 6,670,461, 7,053,207).

In another embodiment, the disclosure features conjugates and/or complexes of nucleobase polymers. Such conjugates and/or complexes can be used to facilitate delivery of polymers into a biological system, such as a cell. Contemplated conjugates include those with cell penetrating peptide. The conjugates and complexes provided may impart therapeutic activity by transferring therapeutic compounds across cellular membranes, altering the pharmacokinetics, and/or modulating the localization of nucleic acid molecules. In general, the transporters described are designed to be used either individually or as part of a multi-component system, with or without degradable linkers. These compounds improve delivery and/or localization of nucleic acid molecules into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

In another aspect a nucleobase polymers comprises one or more 5' and/or a 3'-cap structure. A "cap structure" refers to chemical modifications, which have been incorporated at either terminus of the oligonucleotide. See, for example, Adamic et al., U.S. Pat. No. 5,998,203. These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, polyethylene glycol, alkyl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, Tetrahedron 49, 1925).

In one embodiment, the disclosure features modified nucleobase polymer, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions.

Pharmaceutical Compositions

In certain embodiments, the disclosure contemplates pharmaceutical composition comprising a nucleobase polymer disclosed herein and a pharmaceutically acceptable excipient.

In certain embodiments, the pharmaceutical composition is in the form of a sterilized pH buffered aqueous salt solution or an isotonic aqueous buffer solution.

In certain embodiments, the pharmaceutically acceptable excipient is a propellant or aerosolizing agent. In certain embodiments, the propellant or aerosolizing agent is a hydrofluoroalkane, 1,1,1,2-tetrafluoroethane, 1,1,1,2,3,3,3-heptafluoropropane, propane, n-butane, isobutene, carbon dioxide, compressed air, nitrogen, nitrous oxide, dimethyl ether, trans-1,3,3,3-tetrafluoroprop-1-ene, or combinations thereof.

In certain embodiments, the pharmaceutically acceptable excipient is a lipid, fatty acid, phospholipid, diacyl phospholipid, phosphatidyl choline, sorbitan monopalmitate, polyethyoxylated sorbitan monopalmitate, sucrose stearate (mono- and di-ester), alginate, copolymer of poly(lactide-co-glycolide) (PLGA), poly(vinyl alcohol), or poly(L-lysine) (PLL).

In certain embodiments, the pharmaceutical compositions may be stored in a nebulizer, inhaler, or other container optionally sealed or under a pressure for propelling the pharmaceutical agent(s). The container may contain a spraying apparatus that is manually-actuated or pressurized. Metered dose inhalers (MDIs) typically have a handheld aerosol canister that, upon being pushed, releases an amount of medicine to inhale. Dry powder inhalers (DPIs) do not use a propellant to release the medicine. Instead, a dry powder form of the peptide or agent is drawn into your lungs after a breath. In certain configurations, a container comprising the peptide or agent is inserted a device. Pressing a button or section on the device pierces the container. One can breathe in the powder contained in the container through a mouthpiece on the device.

In certain embodiments, the pharmaceutical compositions disclosed herein further comprise a respiratory agent selected from a glucocorticoid receptor agonist (steroidal and non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, alclometasone dipropionate; a p38 antagonist such as losmapimod; a phosphodiesterase (PDE) inhibitor such as a methylxanthanine, theophylline, and aminophylline; a selective PDE isoenzyme inhibitor, a PDE4 inhibitor and the isoform PDE4D, such as tetomilast, roflumilast, oglemilast, ibudilast, ronomilast; a modulator of chemokine receptor function such as vicriviroc, maraviroc, cenicriviroc, navarixin; a leukotriene biosynthesis inhibitor, 5-lipoxygenase (5-LO) inhibitor, and 5-lipoxygenase activating protein (FLAP) antagonist such as TA270 (4-hydroxy-1-methyl-3-octyloxy-7-sinapinoylamino-2(1H)-quinolinone) such as setileuton, licofelone, quiflapon, zileuton, zafirlukast, or montelukast; and a myeloperoxidase antagonist such as resveratrol and piceatannol.

Effective doses may be extrapolated from dose-response curves derived from in vitro or animal model test systems.

For nucleobase polymers or particles disclosed herein, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Further, the dosage and frequency of administration of nucleobase polymers or particles disclosed herein may be reduced by enhancing uptake and tissue penetration of the nucleobase polymers or particles disclosed herein by modifications such as, for example, lipidation.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with nucleobase polymers or particles disclosed herein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiment, this disclosure contemplates pharmaceutical compositions comprising nucleobase polymers or particles disclosed herein and pharmaceutically acceptable excipient. In certain embodiments, this disclosure contemplates the production of a medicament comprising nucleobase polymers or particles disclosed herein and uses for methods disclosed herein.

In certain embodiments, the disclosure relates to pharmaceutical compositions comprising nucleobase polymers or particles disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil) and injectable organic esters such as ethyl oleate.

Prevention of the action of microorganisms may be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Liquid dosage forms for oral administration include pharmaceutically acceptable emulsions, solutions, suspensions, syrups, and elixirs. In addition to the nucleobase polymers or particles disclosed herein, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

In certain embodiments, production processes are contemplated which two components, nucleobase polymers or particles disclosed herein and a pharmaceutical carrier, are provided already in a combined dry form ready to be reconstituted together. In other embodiments, it is contemplated that nucleobase polymers or particles disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the nucleobase polymers or particles disclosed herein can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as inhalers, syringes, vials, tubes, etc. The pharmaceutical composition may then be applied via actuation or specific needles of the syringe or via suitable catheters. A typical diluent comprises water for injection, and NaCl (preferably 50 to 150 mM, especially 110 mM), $CaCl_2$) (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, this disclosure contemplates a kit comprising a pharmaceutical composition disclosed herein such as a peptide or agent and a container optionally with a suitable diluent. Further components of the kit may be instructions for use, administration means, such as inhalers, syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

Methods of Use

Chronic inflammations constitute an increasing medical problem area of high socioeconomic significance. In certain embodiments, the disclosure relates to methods of treating an inflammatory disease or chronic inflammation comprising administering an effective amount of a nucleobase polymer disclosed herein to a subject in need thereof. In certain embodiments, the inflammatory disease is a respiratory disorder. In certain embodiments, the subject is diagnosed with, exhibiting symptoms of or at risk of asthma, bronchitis, emphysema, chronic obstructive pulmonary disease, laryngitis, or cystic fibrosis.

In certain embodiments, the inflammatory disease is ulcerative colitis.

In certain embodiments, the chronic inflammation is due to autoimmune diseases and diseases from the area of rheumatic diseases (manifestations among others on the skin, lungs, kidneys, vascular system, nervous system, connective tissue, locomotor system, endocrine system), immediate-type allergic reactions and asthma, chronic obstructive lung diseases (COPD), arteriosclerosis, psoriasis and contact eczema and chronic rejection reactions after organ and bone marrow transplants.

EXAMPLES

Dz-Conjugated to Nanoparticles Readily Enter Cells In Vitro and In Vivo

To test the activity of GATA-3 DzNPs, 3'thiol modified GATA-3 Dzs were synthesized. Approximately 100 copies of the Dzs were functionalized onto a gold nanoarticle. PAGE demonstrated that these DzNPs were highly active. To test whether DzNPs could be delivered to the lung, the Dzs were tagged with Cy5 dye to generate fluorescent DzNPs. These particles were administered by nebulization into 4-6 micrometer sized aerosol droplets using a bias flow commercial nebulization system. Fluorescence imaging of the mouse lung showed even and distal distribution 24 hrs after nebulization (FIG. 1).

Figure 2:
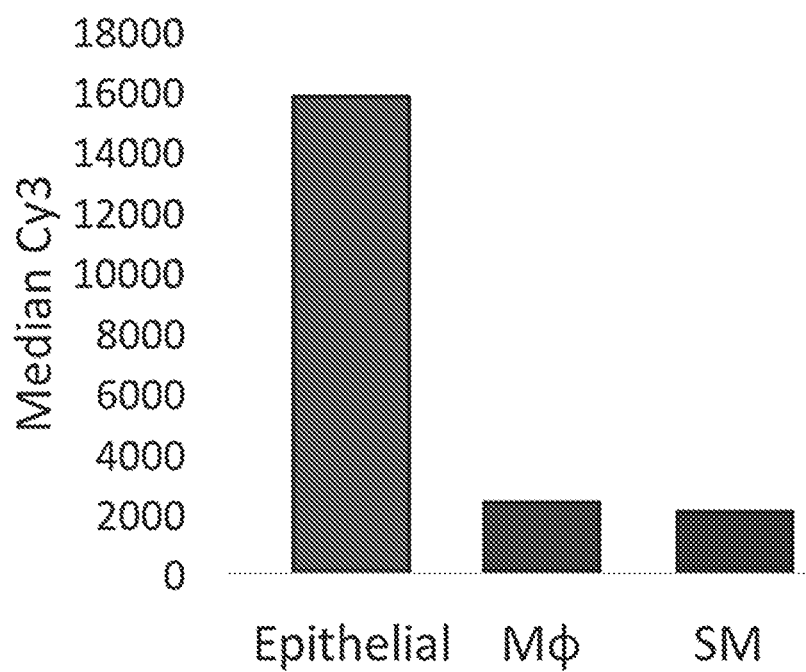
FIG. 2 shows a plot quantifying the uptake of DzNPs in lung resident cell lines. The data was collected using flow cytometry following incubation with 10 nM concentrations of Cy5-labeled DzNPs in epithelial, macrophage, and smooth muscle cells. Cells were incubated in standard serum-containing media for 24 hours without the use of any transfection agent. Flow cytometry confirms resident lung cell uptake of DzNPs.

To confirm resident lung cells can internalize DzNP conjugates, uptake in cultured lung cell lines was tested. The lung cell lines tested were macrophages, smooth muscle cells, as well as epithelial cells. DzNP particles were prepared that were modified with the Cy5 dye, and these particles were incubated at 10 nM concentration for 36 hrs. The cells were cultured in standard serum-containing media. Cells were washed and analyzed using flow cytometry (FIG. 2). The results clearly show a significant level of cellular uptake, with epithelial cells showing the highest level of uptake. Fluorescence microscopy confirmed that the particles were internalized.

DzNPs for GATA-3 Gene Regulation are Active In Vivo

Figure 3A:
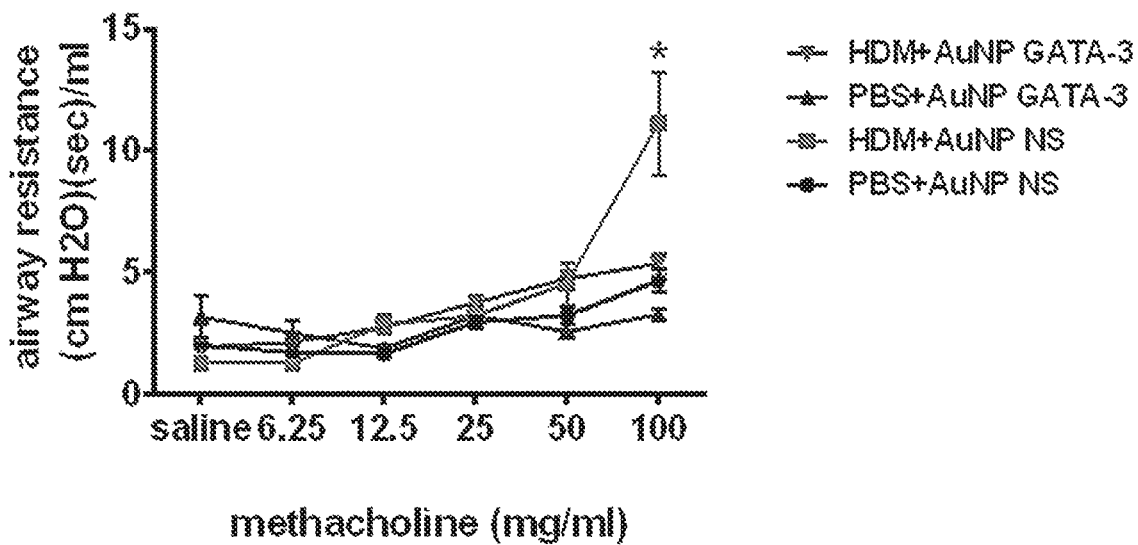
FIG. 3A shows the results of performing a pulmonary function test on four groups of animals. Two groups received daily doses of the house dust mite (HDM) allergen for two weeks, while two groups were control animals and did not receive the HDM. This allergen induced airway resistance in mice and recapitulates the pathophysiology of asthma. Animals received either daily doses of the active DzNPs or an inactive DzNP. The plot shows the raw data measuring the airway resistance as a function of a methacholine challenge. There were three animals in each group.
Figure 3B:
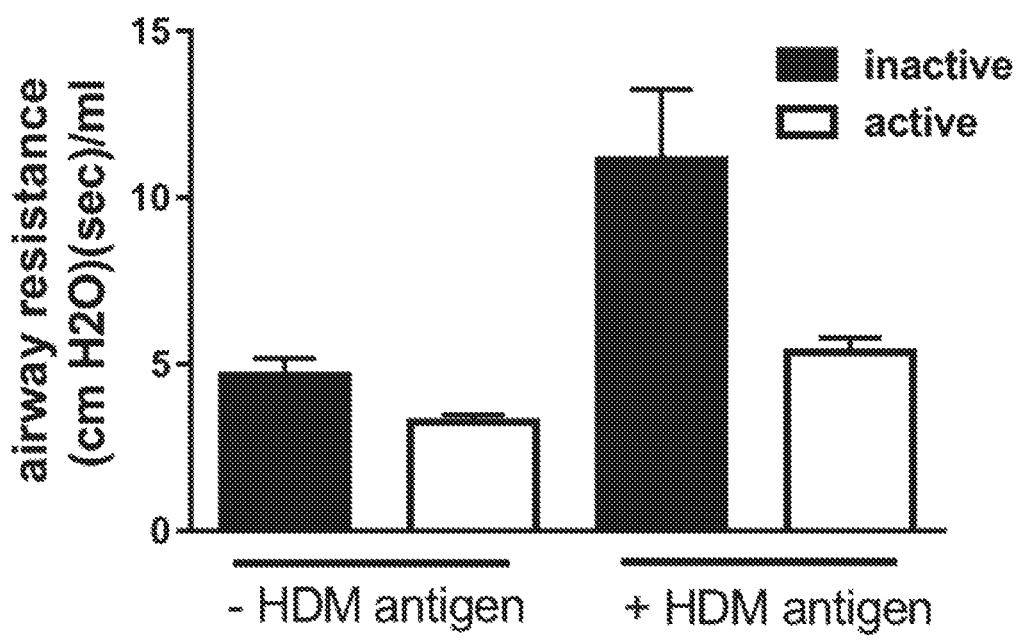
FIG. 3B shows data summarizing the efficacy of active GATA-3 Dz compared to non-specific (NS) DzNPs when challenged with 100 mg/ml methacholine. House dust mite (HDM) extract (50 ug) was inhaled via nebulization daily for 5 days. AuNP (20 ul) administered intranasally (100 nM of DzNPs).

A model of mouse asthma was used to test the efficacy of the DzNPs and showed a significant improvement in airway function for the treated animals as well as reduced cytokine levels in the blood plasma (FIGS. 3A and B). In this model, animals are treated with house dust mite ion a daily basis. The house dust mite antigen exposure model mimics the Th2 inflammation and airway hyper-responsiveness seen in asthma. Der p1 house dust mite extract (50 µg) was administered for 2 weeks. DzNP treatment (100 nM, 20 uL) was delivered intranasally for 5 days (the last week of the experiment). The results of the animal experiments demonstrate that the control group did not show any negative effects due to the nanoparticle treatment. The group receiving the active DzNP showed airway resistance that is similar to that of the untreated animal group. Importantly, the oligonucleotide dose with the DzNP construct was one order of magnitude smaller than that used for soluble Dz experiments. These results are promising and suggest that DzNP based targeting of GATA-3 in the lung offers potential for treating asthma. This experiment was conducted using the HGD40 sequence (site 917 on the human mRNA transcript for GATA-3, SEQ ID NO: 50, (TGGATGGAGGCTAGC-TACAACGAGTCTTGGAG) that was previously identified and also tested in phase II human trials. DNAzyme sequences were screened to identify ones that could be more active than the HGD40 sequence. In vivo efficacy of DzNP were tested for improvements.

In Silico Screen to Discover Active DNAzyme

A computational algorithm was created to predict the most efficient DNAzyme sequences to destroy any given mRNA sequence. The algorithm first scans the entire gene transcript identifying regions of minimal secondary structure by leveraging the mFold software package. NCBI Reference Sequence: NM_001002295.1 for the human mRNA and NCBI Reference Sequence: NM_008091.3 was used for the mouse gene. Next, purine-pyrimidine junctions were identified where the 10-23 DNAzyme is most active. Subsequently, the left and right arms of the DNAzyme are tuned such that the delta G of hybridization is between −8 and −10 kcal/mol. For example, G-C rich regions (~5-7 mer) will tend to have shorter arms, while A-T rich regions require longer arms (~10-12 mer). This screen generates a list of potential DNAzyme targets. The list can then be further filtered based on comparing the human and murine genomes and also various splice variants of a given transcript.

A screen was performed on the potential DNAzyme sites. The top ranked sequences were determined using the algorithm, and these were custom synthesized (see table below). The first column is the location of purine-uracil site that will be cleaved in the human transcript. All of these sequences are shared between mouse and human (albeit at different locations). The sequence in the far right are the DNAzyme sequences used to generate the DzNP conjugates

TABLE 1

DNAzyme hits that target GATA--3 mRNA

| Human GATA-3 cleavage site (b) | 3'b | 5'b | Sequence |
| --- | --- | --- | --- |
| 1461 | 7 | 9 | 5-TGGGCTTAAGGCTAGCTACAACGAGAGGGGC-3 SEQ ID NO: 1 |
| 1519 | 8 | 8 | 5-TGGTCTGAGGCTAGCTACAACGAAGTTCGCA-3 SEQ ID NO: 2 |
| 1606 | 8 | 11 | 5-GTCTGTTAATAGGCTAGCTACAACGATGTGAAGC-3 SEQ ID NO: 3 |
| 1662 | 8 | 9 | 5-TGCTAGACAGGCTAGCTACAACGATTTTCGGT-3 SEQ ID NO: 4 |
| 1664 | 9 | 9 | 5-TTTGCTAGAGGCTAGCTACAACGAATTTTCGG-3 SEQ ID NO: 5 |
| 1673 | 9 | 9 | 5-CTTTTTGGAGGCTAGCTACAACGATTGCTAGAC-3 SEQ ID NO: 6 |
| 1682 | 10 | 9 | 5-TTTTTTGCAGGCTAGCTACAACGATTTTTGGATT-3 SEQ ID NO: 7 |
| 1970 | 8 | 9 | 5-GCTTCATGAGGCTAGCTACAACGAACTGCTCC-3 SEQ ID NO: 8 |
| 1973 | 9 | 8 | 5-AGGCTTCAGGCTAGCTACAACGAGATACTGCT-3 SEQ ID NO: 9 |
| 2093 | 8 | 10 | 5-GGCTTATTCAGGCTAGCTACAACGAAGATGGGG-3 SEQ ID NO: 10 |
| 2097 | 9 | 9 | 5-AATGGCTTAGGCTAGCTACAACGATCACAGATG-3 SEQ ID NO: 11 |
| 2114 | 9 | 9 | 5-TAGGGATAGGCTAGCTACAACGAGAGTCAGAA-3 SEQ ID NO: 12 |
| 2116 | 9 | 9 | 5-AATAGGGAGGCTAGCTACAACGAATGAGTCAG-3 SEQ ID NO: 13 |
| 2133 | 10 | 9 | 5-CACTAGAGAGGCTAGCTACAACGACCTGTTAAAT-3 SEQ ID NO: 14 |
| 2140 | 9 | 8 | 5-TCACAGCAGGCTAGCTACAACGATAGAGACCC-3 SEQ ID NO: 15 |
| 2145 | 9 | 10 | 5-TTTTTTTCAGGCTAGCTACAACGAAGCACTAGA-3 SEQ ID NO: 16 |
| 2157 | 11 | 8 | 5-GTTCAGCAGGCTAGCTACAACGATTTTTTTTCA-3 SEQ ID NO: 17 |
| 2171 | 9 | 12 | 5-ATATAAGTTATAGGCTAGCTACAACGAGCAATGTTC-3 SEQ ID NO: 18 |

TABLE 1-continued

DNAzyme hits that target GATA-3 mRNA

| Human GATA-3 cleavage site (b) | 3'b | 5'b | Sequence |
|---|---|---|---|
| 2173 | 9 | 12 | 5-CAATATAAGTTAGGCTAGCTACAACGAATGCAATGT-3<br>SEQ ID NO: 19 |
| 2251 | 8 | 10 | 5-ATTCCTTAAAGGCTAGCTACAACGATTCTTGGC-3<br>SEQ ID NO: 20 |
| 2326 | 8 | 10 | 5-GGAAACAAAAGGCTAGCTACAACGATGGCAGTT-3<br>SEQ ID NO: 21 |
| 2331 | 9 | 9 | 5-GAAAGGAAAGGCTAGCTACAACGAAAAACTGGC-3<br>SEQ ID NO: 22 |
| 2363 | 9 | 11 | 5-TTTTCTTTTAAGGCTAGCTACAACGAGCATCAAAC-3<br>SEQ ID NO: 23 |
| 2560 | 8 | 10 | 5-ACAACAATTAGGCTAGCTACAACGAAGGGACTT-3<br>SEQ ID NO: 24 |
| 2563 | 9 | 10 | 5-CAAACAACAAGGCTAGCTACAACGATACAGGGAC-3<br>SEQ ID NO: 25 |
| 2566 | 10 | 10 | 5-ATACAAACAAGGCTAGCTACAACGAAATTACAGGG-3<br>SEQ ID NO: 26 |
| 2569 | 10 | 10 | 5-TACATACAAAGGCTAGCTACAACGAACAATTACA-3<br>SEQ ID NO: 27 |
| 2575 | 9 | 11 | 5-TGAATTATACAGGCTAGCTACAACGAACAAACAAC-3<br>SEQ ID NO: 28 |
| 2577 | 10 | 11 | 5-TTTGAATTATAGGCTAGCTACAACGAATACAAACAA-3<br>SEQ ID NO: 29 |
| 2597 | 8 | 10 | 5-TCTTTTCTTAGGCTAGCTACAACGATTGGTGC-3<br>SEQ ID NO: 30 |
| 2607 | 11 | 11 | 5-ATAAATCTACAGGCTAGCTACAACGACTTTTCTTATT-3<br>SEQ ID NO: 31 |
| 2609 | 10 | 11 | 5-AAATAAATCTAGGCTAGCTACAACGAATCTTTTCTT-3<br>SEQ ID NO: 32 |
| 2622 | 11 | 12 | 5-TGTATAATATGAGGCTAGCTACAACGAGAAATAAATCT-3<br>SEQ ID NO: 33 |
| 2625 | 11 | 11 | 5-TCTGTATAATAGGCTAGCTACAACGAGATGAAATAAA-3<br>SEQ ID NO: 34 |
| 2627 | 10 | 10 | 5-GTCTGTATAAGGCTAGCTACAACGAATGATGAAAT-3<br>SEQ ID NO: 35 |
| 2644 | 8 | 11 | 5-AATTTATACAAGGCTAGCTACAACGAAGTTCGGT-3<br>SEQ ID NO: 36 |
| 2647 | 9 | 13 | 5-AAATAAATTTATAGGCTAGCTACAACGAAACAGTTCG-3<br>SEQ ID NO: 37 |
| 2649 | 9 | 12 | 5-TAAATAAATTTAGGCTAGCTACAACGAACAACAGTT-3<br>SEQ ID NO: 38 |
| 2653 | 10 | 11 | 5-CAGTAAATAAAGGCTAGCTACAACGATTATACAACA-3<br>SEQ ID NO: 39 |
| 2657 | 11 | 9 | 5-AGCAGTAAAGGCTAGCTACAACGAAAATTTATACA-3<br>SEQ ID NO: 40 |
| 2668 | 9 | 10 | 5-GTTCTTAAGAGGCTAGCTACAACGATAGCAGTAA-3<br>SEQ ID NO: 41 |
| 2723 | 9 | 10 | 5-CAACCAAAAAGGCTAGCTACAACGATGAGAGAGA-3<br>SEQ ID NO: 42 |

TABLE 1-continued

DNAzyme hits that target GATA--3 mRNA

| Human GATA-3 cleavage site (b) | 3'b | 5'b | Sequence |
|---|---|---|---|
| 2827 | 12 | 10 | 5-TTAGAAGCTAGGCTAGCTACAACGATTAATAAATATC-3<br>SEQ ID NO: 43 |
| 2910 | 8 | 9 | 5-TGACATGCAGGCTAGCTACAACGAGCTGGTAG-3<br>SEQ ID NO: 44 |
| 2986 | 8 | 9 | 5-TCACTAACAGGCTAGCTACAACGAAGAACACG-3<br>SEQ ID NO: 45 |
| 2988 | 9 | 10 | 5-TGATCACTAAGGCTAGCTACAACGAACAGAACAC-3<br>SEQ ID NO: 46 |
| 3017 | 10 | 10 | 5-ATTATTCCAAGGCTAGCTACAACGAAGACTGTATT-3<br>SEQ ID NO: 47 |
| 3048 | 12 | 11 | 5-AAATATTTTCAGGCTAGCTACAACGATTTATTATTATG-3<br>SEQ ID NO: 48 |
| 3056 | 10 | 11 | 5-TAGTTTTAAAAGGCTAGCTACAACGAATTTTCACTT-3<br>SEQ ID NO: 49 |

Experimental Screening of DNAzymes.

Figure 4A:
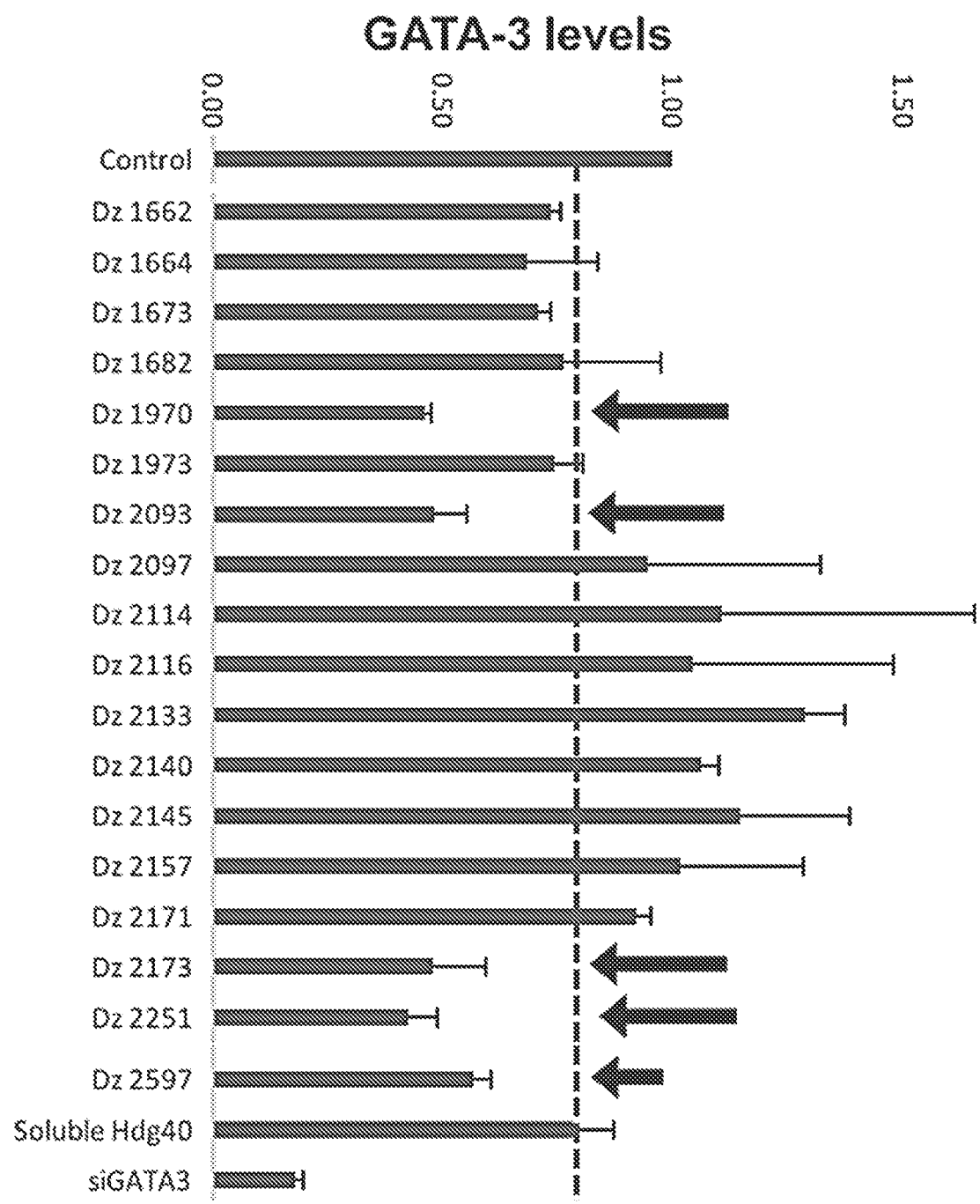
FIG. 4A shows RT-PCR quantification of GATA-3 expression levels in cell lines following DNAzyme treatment. The screen shows DNAzymes that are more active than HGD40. The dotted line indicates the GATA-3 levels in HGD40 sequence treated cells. Arrows indicate the DNAzyme sequences that showed lower levels of GATA-3 compared to the soluble HGD40 sequence is SEQ ID NO: 50. All of the DNAzymes have a 3'-end $T_{10}$ modification.
Figure 4B:
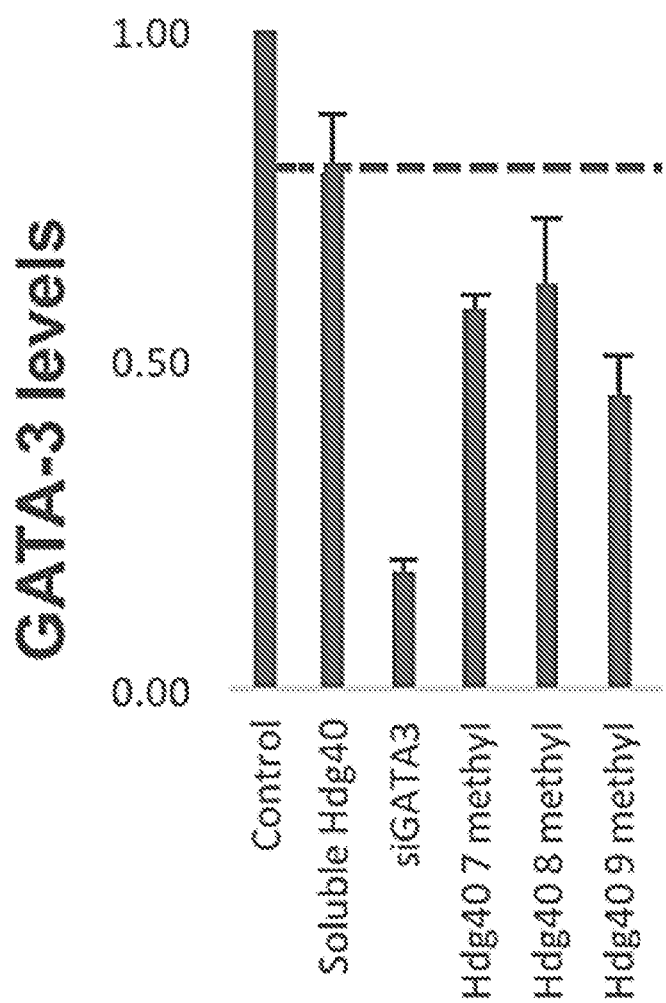
FIG. 4B shows RT-PCR quantification of GATA-3 expression levels in cells treated with with HGD40 sequence with certain modifications. HGD40 9 methyl refers to SEQ ID NO: 53, (G*-T*-G*-G*-dA-dT-dG-dG-dA-dG-dG-dC-dT-dA-dG-dC-dT-dA-dC-dA-dA-dC-dG-dA-dG-dT-dC-dT-dT-G*-G*-A*-G*-$T_{10}$-3'-3'T) wherein d is deoxy and * is 2'-O-methyl ribose. HGD40 8 methyl refers to SEQ ID NO: 54, (T*-G*-G*-A*-dT-dG-dG-dA-dG-dG-dC-dT-dA-dG-dC-dT-dA-dC-dA-dA-dC-dG-dA-dG-dT-dC-dT-T*-G*-G*-A*-$T_{10}$-3'-3'T) wherein d is deoxy and * is 2'-O-methyl ribose. HGD40 7 methyl refers to SEQ ID NO: 55, (G*-G*-A*-T*-dG-dG-dA-dG-dG-dC-dT-dA-dG-dC-dT-dA-dC-dA-dA-dC-dG-dA-dG-dT-dC-T*-T*-G*-G*-$T_{10}$-3'-3'T) wherein d is deoxy and * is 2'-O-methyl ribose.

DNAzyme sequences were screened for activity using RT-PCR in T47D breast cancer cell lines that are known to express high levels of the GATA-3 mRNA (FIG. 4). Each oligonucleotide was incubated with the cells for 24 hours prior to collect mRNA, reverse transcription and then running RT-PCR. Lipofectamine delivery was performed using of the soluble oligonucleotides. The expression levels were normalized and the data analyzed using standard methods. Each experiment was run in triplicate, and each well was analyzed several times to obtain the mean GATA-3 expression level in each sample. Several of the tested sequences showed activity that was greater than HGD-40.

Screening of Gold Nanoparticle DNAzymes Conjugates

Figure 5:
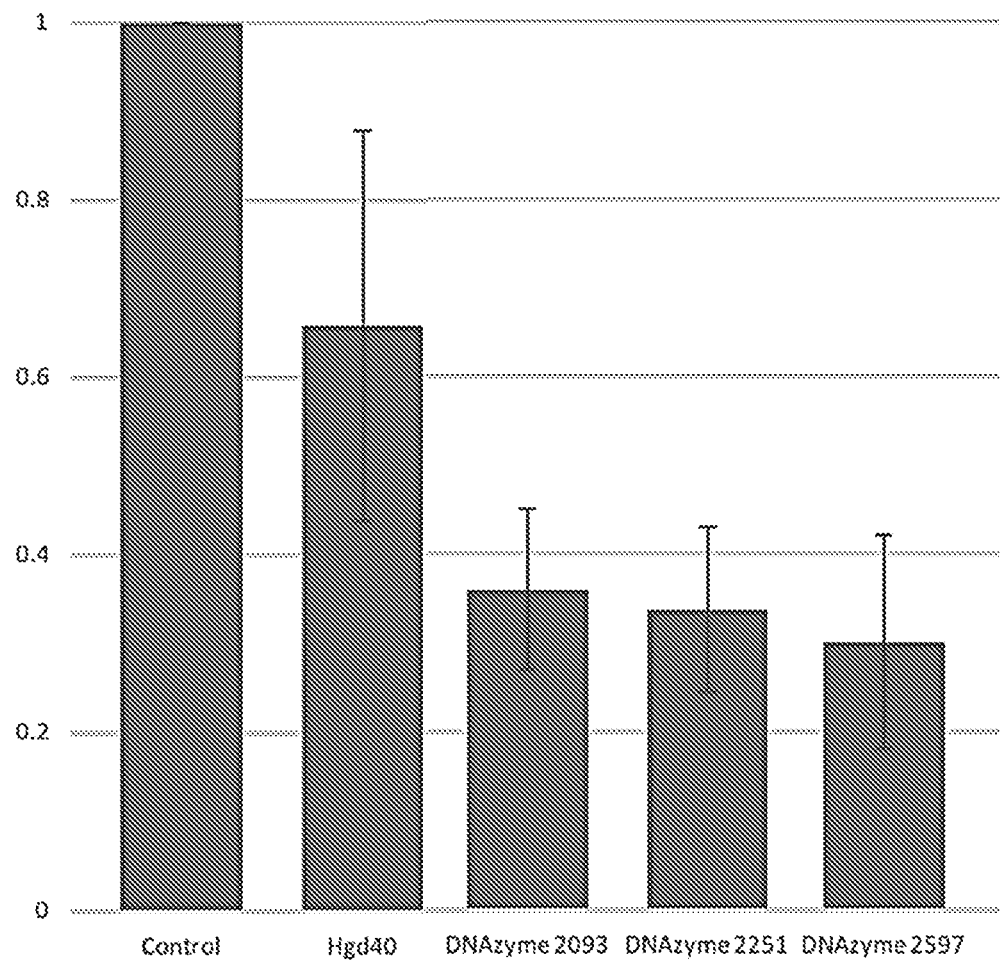
FIG. 5 shows RT-PCR data on GATA-3 expression levels following DNAzyme-AuNP treatment (10 nM for 24 hrs). Several DzNPs were shown to be more active than HGD40-NPs.
Figure 6A:
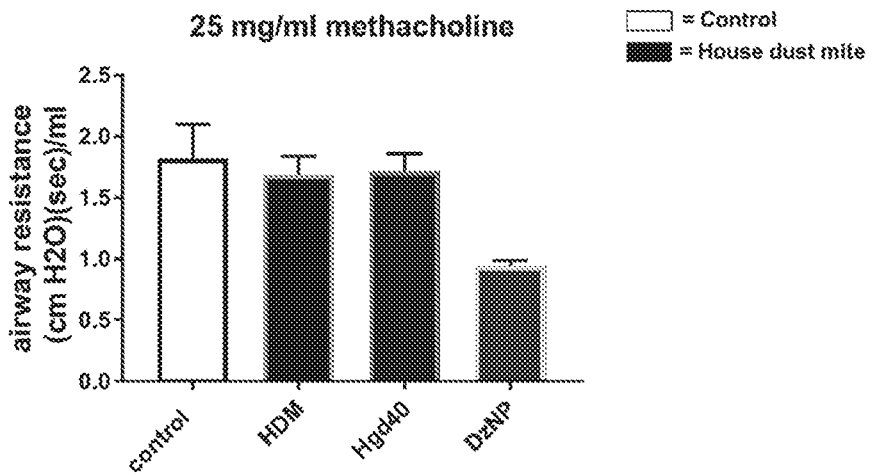
FIG. 6A shows the results of performing a pulmonary function test on the HDM model of mouse asthma. There were four groups of animals with three animals within each group. One group did not receive the HDM allergen and was considered as a control. The second group received the HDM allergen for 3 weeks and was not rescued using the DzNP drug treatment. The third group received the HGD40-NP along with the HDM allergen. The final group received the DzNP with Dz2251 along with the HDM allergen. The animals were challenged using 25 mg/mL methacholine. Airway resistance was measured in mouse model of asthma. The DzNP were delivered intranasally for 2 weeks (100 nM, 20 uL daily).
Figure 6B:
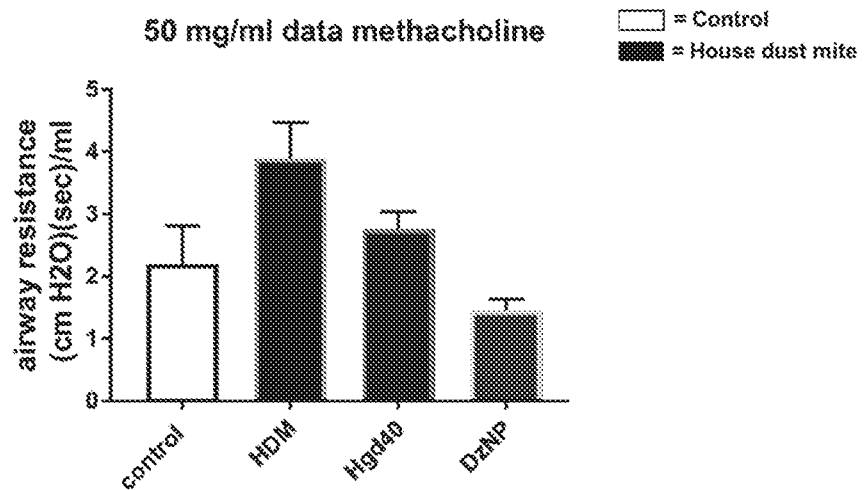
FIG. 6B shows data using 50 mg/mL methacholine.
Figure 6C:
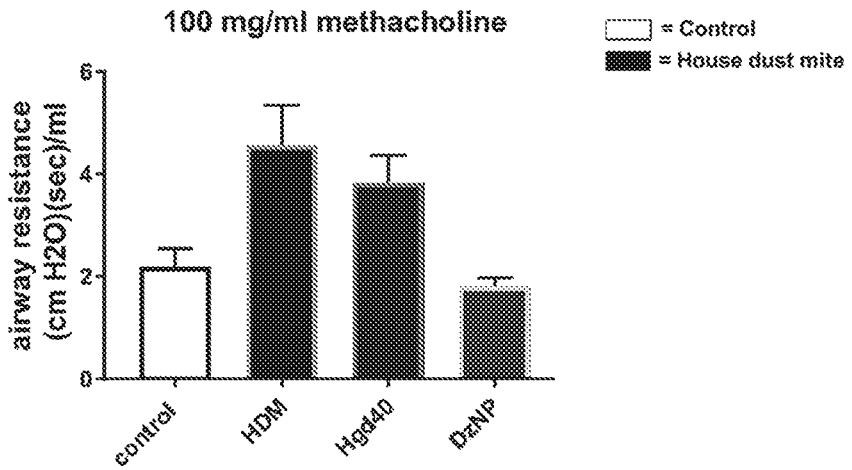
FIG. 6C shows data using 100 mg/mL methacholine.
Figure 7:
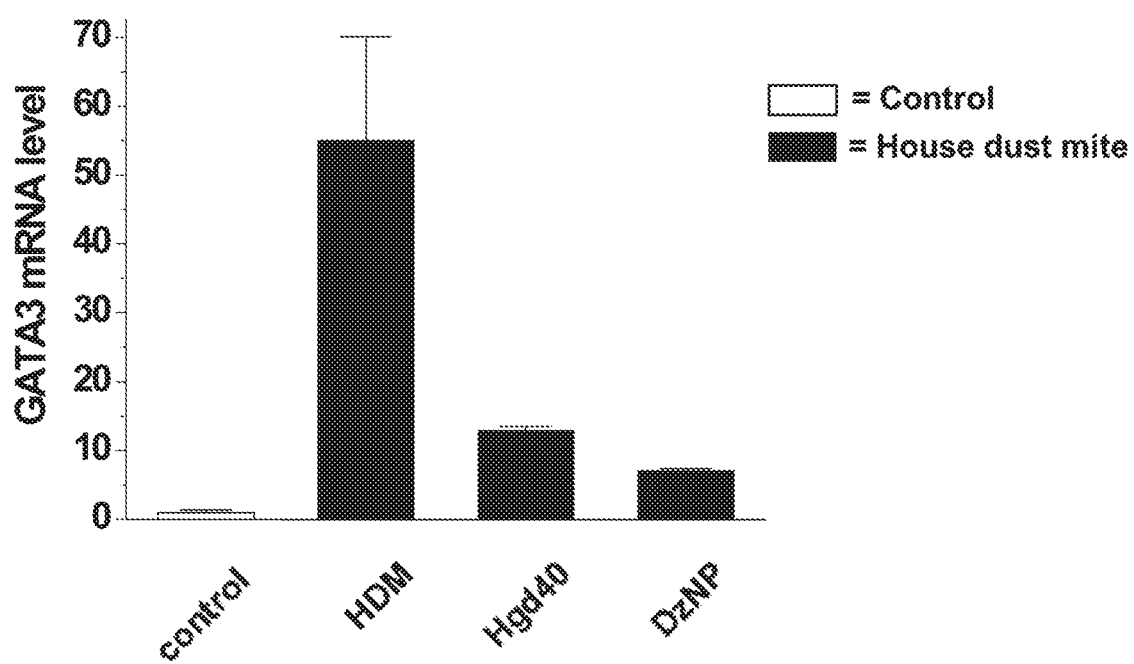
FIG. 7 plots RT-PCR levels of GATA-3 mRNA in the lungs of the animals (from FIG. 6).

Activity of the top DzNP conjugates were tested and compared against a HGD-40 DzNP. FIG. 5 show the results of the screen and confirm that several of the hits were indeed more potent than HGD40. All the DzNP samples were prepared at 10 nM concentration and incubated in standard serum-containing cell media for 24 hrs prior to measuring mRNA levels.

Dz2251-NP Conjugates is Active In Vivo

Animal studies were performed to compare the activity of HGD40 DzNPs against Dz2251 DzNPs (FIG. 6A-C and FIG. 7). The house dust mite antigen model of mouse asthma was used. Four groups of animals were tested. The first group were untreated with antigen and show baseline airway resistance when the animals were challenged with methacholine. The second group received the house dust mite antigen but did not receive any DNAzyme treatments. The third and fourth groups were treated with both the allergen as well as the HGD40-DzNP and the Dz2251 DzNP, respectively. The results are consistent with findings that indicate that HGD40 DzNP is active in improvement airway function. Importantly, Dz2251 showed a higher level of efficacy at all levels of methacholine challenge. Dz2251 also showed greater GATA-3 mRNA knockdown in vivo. These results indicate that Dz2251-DzNPs are more active in treating the Th2 endotype of asthma as well as other inflammatory diseases such as ulcerative colitis.

The invention claimed is:

1. A nucleobase polymer comprising a sequence selected from SEQ ID NO: 1-49.

2. The nucleobase polymer of claim 1 having SEQ ID NO: 10 (GGCTTATTCAGGCTAGCTACAACGAAGATGGGG), SEQ ID NO: 20 (ATTCCTTAAAGGCTAGCTACAACGATTCTTGGC), or SEQ ID NO: 30 (TCTTTTCTTAGGCTAGCTACAACGATTTGGTGC).

3. A nanoparticle coated with a nucleobase polymer comprising a sequence that cleaves RNA and linked to flanking 5' and 3' nucleobase sequences that hybridize with SEQ ID NO: 52, wherein the sequence is selected from SEQ ID NO: 1-49.

4. The nanoparticle of claim 3 wherein the nucleobase polymer is SEQ ID NO: 10 (GGCTTATTCAGGCTAGCTACAACGAAGATGGGG), SEQ ID NO: 20 (ATTCCTTAAAGGCTAGCTACAACGATTCTTGGC), or SEQ ID NO: 30 (TCTTTTCTTAGGCTAGCTACAACGATTTGGTGC).

5. A liquid particle comprising a nanoparticle of claim 3, wherein the liquid particle has a diameter of between 0.5 microns and 10 microns.

6. A pharmaceutical composition comprising a nanoparticle of claim 3 and a pharmaceutically acceptable excipient.

7. The pharmaceutical composition of claim 6, comprising a pH buffered aqueous salt solution.

8. The pharmaceutical composition of claim 6, wherein the pharmaceutically acceptable excipient is a hydrofluoroalkane, 1,1,1,2-tetrafluoroethane, 1,1,1,2,3,3,3-heptafluoropropane, propane, n-butane, isobutene, carbon dioxide, nitrogen, nitrous oxide, dimethyl ether, or trans-1,3,3,3-tetrafluoroprop-1-ene.

9. A container comprising a nanoparticle of claim 3.

10. The container of claim 9 further comprising a propellant.

11. The container of claim 9 configured with a spraying or misting apparatus, mouthpiece, or facemask.

* * * * *